(12) United States Patent
Eun et al.

(10) Patent No.: US 12,170,148 B2
(45) Date of Patent: Dec. 17, 2024

(54) LEARNING PLATFORM FOR PATIENT JOURNEY MAPPING

(71) Applicant: Janssen Pharmaceuticals, Inc., Titusville, NJ (US)

(72) Inventors: Ye Jin Eun, Princeton, NJ (US); Wei Wang, Berwyn, PA (US); Xiaoying Wu, Upper Holland, PA (US); Jun Morimura, Tokyo (JP); Geoffrey Townsend Red, Devon, PA (US)

(73) Assignee: Janssen Pharmaceuticals, Inc., Titusville, NJ (US)

( * ) Notice: Subject to any disclaimer, the term of this patent is extended or adjusted under 35 U.S.C. 154(b) by 579 days.

(21) Appl. No.: 16/937,441

(22) Filed: Jul. 23, 2020

(65) Prior Publication Data

US 2021/0027896 A1 Jan. 28, 2021

Related U.S. Application Data

(60) Provisional application No. 62/878,174, filed on Jul. 24, 2019.

(51) Int. Cl.
*G16H 50/70* (2018.01)
*A61B 5/00* (2006.01)
(Continued)

(52) U.S. Cl.
CPC .......... *G16H 50/70* (2018.01); *A61B 5/7267* (2013.01); *G16H 10/60* (2018.01); *G16H 15/00* (2018.01);
(Continued)

(58) Field of Classification Search
CPC ........ G16H 50/70; G16H 10/60; G16H 15/00; G16H 50/20; G16H 50/50; G16H 70/20;
(Continued)

(56) References Cited

U.S. PATENT DOCUMENTS 10,061,894 B2 8/2018 Sethumadhavan et al.
11,250,950 B1 * 2/2022 Miller ................... G06F 18/214
(Continued)

OTHER PUBLICATIONS

KIPO—Notification and International Search Report and Written Opinion for related International Appln. No. PCT/IB2020/056971 mailed Oct. 29, 2020; 13 pgs.
(Continued)

*Primary Examiner* — Chad A Newton
(74) *Attorney, Agent, or Firm* — McDermott Will & Emery LLP

(57) ABSTRACT

Various aspects of the subject technology relate to systems, methods, and machine-readable media for a learning platform that employs machine learning to identify patterns that describe meaningful subgroups of patients associated with a particular disease, distinct characteristics of each subgroup, and implications of belonging to a specific subgroup in terms of developing into a more severe disease state for patient journey mapping. The system may include a mapping server that includes a medical-event embedding engine that embeds electronic health records into vectors, a clustering engine that identifies clusters of patients with similar patient journeys by operating on the output of the medical-event embedding engine, and a cluster profiling engine that identifies distinguishing medical events for each identified cluster by operating on the output of the clustering engine.

12 Claims, 14 Drawing Sheets

(51) Int. Cl.
*G16H 10/60* (2018.01)
*G16H 15/00* (2018.01)
*G16H 50/20* (2018.01)
*G16H 50/50* (2018.01)
*G16H 70/20* (2018.01)
*G06Q 50/26* (2012.01)
*G16H 10/20* (2018.01)
*G16H 20/10* (2018.01)

(52) U.S. Cl.
CPC .............. *G16H 50/20* (2018.01); *G16H 50/50* (2018.01); *G16H 70/20* (2018.01); *G06Q 50/26* (2013.01); *G16H 10/20* (2018.01); *G16H 20/10* (2018.01)

(58) Field of Classification Search
CPC ...... G16H 10/20; G16H 20/10; A61B 5/7267; A61B 5/4842; G06Q 50/26; G06F 18/23; G06N 3/04; G06N 3/08; G06N 20/00
See application file for complete search history.

(56) References Cited

U.S. PATENT DOCUMENTS

| | | | | |
|---|---|---|---|---|
| 2002/0022956 | A1* | 2/2002 | Ukrainczyk | G06F 40/20 707/E17.084 |
| 2005/0246324 | A1* | 11/2005 | Paalasmaa | G06F 16/951 |
| 2009/0299766 | A1 | 12/2009 | Friedlander et al. | |
| 2014/0297324 | A1 | 10/2014 | Duftler et al. | |
| 2016/0063213 | A1 | 3/2016 | Blue | |
| 2016/0196398 | A1 | 7/2016 | Vivero et al. | |
| 2017/0116379 | A1 | 4/2017 | Adams et al. | |
| 2017/0312574 | A1* | 11/2017 | Matsuzawa | G16H 20/30 |
| 2018/0068083 | A1* | 3/2018 | Cohen | G16B 50/30 |
| 2018/0268253 | A1* | 9/2018 | Hoffman | G06V 10/761 |
| 2019/0013089 | A1* | 1/2019 | Raghavan | G06Q 10/10 |
| 2019/0297324 | A1 | 3/2019 | Sze et al. | |
| 2020/0064444 | A1* | 2/2020 | Regani | G01S 13/931 |
| 2020/0151519 | A1* | 5/2020 | Anushiravani | G06N 5/01 |
| 2020/0243167 | A1* | 7/2020 | Will | G06N 20/20 |
| 2020/0327444 | A1* | 10/2020 | Negi | G06N 20/00 |

OTHER PUBLICATIONS

Ahlqvist, E., et al., "Novel subgroups of adult-onset diabetes and their association with outcomes: a data-driven cluster analysis of six variables," The Lancet: Diabetes & Endocrinology, May 1, 2018, vol. 6, Issue 5, pp. 361-369—DOI:https://doi.org/10.1016/S2213-8587(18)30051-2.

Bojanowski, P., et al. "Enriching Word Vectors with Subword Information," Transactions of the Association for Computational Linguistics, Jun. 2017, vol. 5, pp. 135-146.

Choi, Y., et al. "Learning Low-Dimensional Representations of Medical Concepts," AMIA Joint Summits on Translational Science proceedings, Jul. 20, 2016, pp. 41-50—PMID: 27570647.

Doshi-Velez, F., et al. "Comorbidity Clusters in Autism Spectrum Disorders: An Electronic Health Record Time-Series Analysis," Pediatrics Jan. 2014, 133 (1) e54-e63; DOI: https://doi.org/10.1542/peds.2013-0819.

Glicksberg, B.S., et al., "PatientExploreR: an extensible application for dynamic visualization of patient clinical history from electronic health records in the OMOP common data model," Bioinformatics, vol. 35, Issue 21, 2019, pp. 4515-4518—DOI: 10.1093/bioinformatics/btz409.

Jeong, Hyemin, et al., "Comorbidities of rheumatoid arthritis: Results from the Korean National Health and Nutrition Examination Survey," PLoS One, Apr. 2017, 12(4):e0176260, pp. 1-15.

Kaul, A, et al. "Systemic lupus erythematosus" Nature Reviews—Disease Primers 2016. vol. 2: 16039 , pp. 1-21.

Mikolov, T., et al., "Distributed Representations of Words and Phrases and their Compositionality," retrieved on Sep. 29, 2020 from https://papers.nips.cc/paper/5021-distributed-representations-of-words-and-phrases-and-their-compositionality.pdf.

Radovanović, M., et al., "Hubs in Space: Popular Nearest Neighbors in High-Dimensional Data," J. of Machine Learning Research, Sep. 2010, vol. 11, pp. 2487-231—Retrieved on Sep. 29, 2020 from https://dl.acm.org/doi/pdf/10.5555/1756006.1953015.

Raterman, H.G., et al., "Rheumatoid arthritis is associated with a high prevalence of hypothyroidism that amplifies its cardiovascular risk," Ann Rheum Dis. Feb. 2008; 67(2):229-32. DOI: 10.1136/ard.2006.068130. Epub Jun. 8, 2007., PMID: 17557891—https://www.ncbi.nlm.nih.gov/pubmed/17557891.

Staykova, N. D., "Rheumatoid Arthritis and thyroid abnormalities," Folia Med (Plovdiv), 2007, 49(3-4), pp. 5-12—PMID: 18504927.

Wang et al., "A Comparison of Word Embeddings for the Biomedical Natural Language Processing," J. Biomed Inform. Nov. 2018, vol. 87, pp. 12-20; doi:10.1016/j.jbi.2018.09.008.

Xiao, C., et al., "Opportunities and challenges in developing deep learning models using electronic health records data: a systematic review," AMIA 2018, vol. 25, Issue 10, pp. 1419-1428. Retrieved from https://www.ncbi.nlm.nih.gov/pmc/articles/PMC6188527/pdf/ocy068.pdf.

Zhang, J., et al., "Patient2Vec: A Personalized Interpretable Deep Representation of the Longitudinal Electronic Health Record," IEEE Access, 2018, vol. 6, pp. 65333-65346—Digital Object Identifier 10.1109/ACCESS.2018.2875677—Retrieved from https://ieeexplore.ieee.org/stamp/stamp.jsp?tp=&arnumber=8490816.

Zhu et al., Measuring Patient Similarities via a Deep Architecture with Medical Concept Embedding. IEEE Computer Society, 2016 pp. 749-758.

Farhan, Wael, et al. "A Predictive Model for Medical Events Based on Contextual Embedding of Temporal Sequences." JMIR Medical Informatics. 2016, vol. 4, Issue 4, 13 pages.

EPO—Extended European Search Report for corresponding European Appl. No. 20844860.5 dated Jun. 28, 2023, 12 pages.

* cited by examiner

LEARNING PLATFORM FOR PATIENT JOURNEY MAPPING

CROSS-REFERENCE TO RELATED APPLICATIONS

The present disclosure is related, and claims priority under 35 U.S.C. § 119(e), to U.S. Provisional Patent Application No. 62/878,174, entitled MACHINE LEARNING FOR PATIENT JOURNEY MAPPING, to Ye Jin Eun et-al. filed on Jul. 24, 2019, the contents of which are hereby incorporated by reference in their entirety, for all purposes.

BACKGROUND

Field

The present disclosure generally relates to a learning healthcare platform, and more particularly to a learning platform that employs machine learning for patient journey pattern discovery.

Description of the Related Art

Many diseases such as Systemic Lupus Erythematosus (SLE) are characterized by a wide spectrum of clinical manifestations, including disease symptoms, comorbidities, and drug-adverse reactions. The heterogeneity in disease progression from one individual patient to another in this type of disease creates a challenge in developing new therapies for these patients, because the complexity hampers identification of patients by healthcare providers, development of inclusion and exclusion criteria for an effective clinical trial design, and retrospective analyses of clinical trials. Understanding how SLE manifestations appear as one or a combination of disease sub types, including skin, kidney, or central nervous system related conditions in different individuals could provide a powerful tool to personalize treatment regimens and identify patients with increased risk of complications at diagnosis for these different disease sub-types.

Conventional approaches employed to provide individualized treatments involve a medical professional matching individual features among patient records, identifying common disease characteristics. Limited by relying on previously identified feature-disease progression mapping, these conventional approaches impose a selection bias, and have been slow to yield needed insight for improving diagnoses, care, therapy development, clinical trial design, implementation, and analysis, particularly for diseases with heterogeneous progressions.

Improved technical tools for leveraging the vast medical records of large numbers of patients to segment their disease progressions into sub-types would accelerate disease diagnosis, care, and R&D process.

SUMMARY

The present disclosure provides a system for identifying and characterizing distinct progression pathways of each of various diseases. The systems and methods disclosed herein provide a uniquely trained and uniquely constructed machine-leaning engine that generates numerical vectors in a continuous vector space that each represent substantially the entire medical history of a patient. This machine-learning engine is further provided within a unique pipeline that includes a clustering engine that identifies clusters of patients with similar patient journeys using the numerical vectors, and a cluster profiling engine that identifies distinguishing features of each cluster. The disclosed systems and methods generate outputs that describe meaningful subgroups of patients associated with a particular disease, distinct characteristics of each subgroup, and implications of belonging to a specific subgroup in terms of developing into a more severe disease state.

According to some aspects of the present disclosure, a computer-implemented method is provided. The method includes providing at least two time-separated medical events from a medical record for each of a plurality of patients in a pre-identified cohort of patients to a medical-event embedding engine of a mapping server, the medical-event embedding engine having parameters trained to cause the medical-event embedding engine to generate an output vector corresponding to a medical event in an input medical record; generating vectors with the medical-event embedding engine by operating on the at least two time-separated medical events for each of the patients in the pre-identified cohort, each vector corresponding to a medical event in the medical record of one of the patients in the pre-identified cohort; combining, with a processor of the mapping server, the generated vectors for each patient in the pre-identified cohort to form a single vector representation of a medical history for each patient in the pre-identified cohort; identifying, with a clustering engine of the mapping server, clusters of the patients in the pre-identified cohort that have similar patient journeys by performing a clustering operation on the single vector representations; identifying, with a cluster profiling engine of the mapping server, differentiating medical events of each of the identified clusters by performing a cluster profiling operation using an output of the clustering engine and the medical records of the patients in the identified clusters; and providing, with the processor and for display, at least relative numbers of the differentiating medical events in at least one of the identified clusters.

According to some aspects of the present disclosure, a computer-implemented method is provided. The method includes receiving, at a mapping server, medical records for a pre-identified cohort of patients, the cohort associated with at least one medical event in the medical records of each of the patients, and each medical record including at least two time-separated medical events; operating on the at least two time-separated medical events with a medical-event embedding engine of the mapping server to generate embedded medical history data for the pre-identified cohort of patients; operating on the embedded medical history data with a clustering engine of the mapping server to identify at least one cluster of the patients in the pre-identified cohort that have similar patient journeys; operating on an output of the clustering engine with a cluster profiling engine of the mapping server to identify differentiating medical events of the at least one cluster of the patients in the pre-identified cohort that have the similar patient journeys; and providing, for display, at least relative numbers of the differentiating medical events of the at least one cluster of the patients in the pre-identified cohort that have the similar patient journeys.

According to some aspects of the present disclosure, a computer-implemented method is provided. The method includes providing, from a mapping server for display on a display of a device, a request for medical records for a pre-identified cohort of patients, the cohort associated with at least one common medical event in the medical records of each of the patients, and each medical record including at least two time-separated medical events; receiving the medical records at the mapping server responsive to the request; identifying, using a medical-event embedding engine within the mapping server operating on the at least two time-separated medical events, at least one cluster of the patients that have similar patient journeys; and providing, for display on the display of the device, at least relative numbers of the medical events of the at least one cluster of the patients that have similar patient journeys.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

Figure 1:
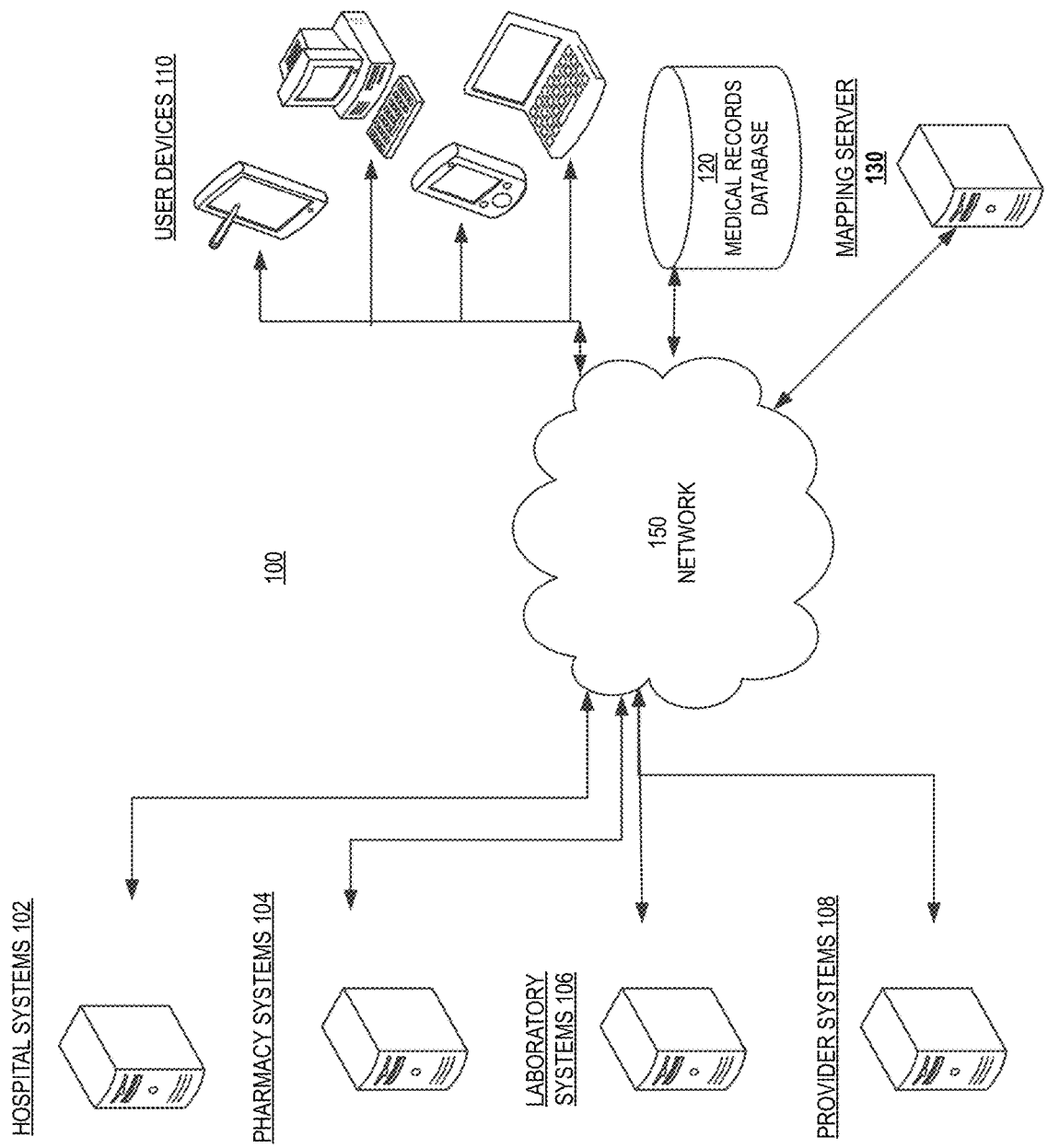
FIG. 1 illustrates an example architecture for machine-learning for patient journey mapping, suitable for practicing some implementations of the disclosure.

In the following detailed description, numerous specific details are set forth to provide a full understanding of the present disclosure. It will be apparent, however, to one ordinarily skilled in the art, that the embodiments of the present disclosure may be practiced without some of these specific details. In other instances, well-known structures and techniques have not been shown in detail so as not to obscure the disclosure.

General Overview

The systems and methods disclosed herein provide a novel computer architecture that combines various existing and new machine-learning and statistical computing tools in an unexpected arrangement of computing elements. This novel computer architecture provides tools to better understand diversity in patient disease journeys, and to decipher factors associated with different disease pathways.

As described in further detail herein, unexpected challenges arose during the process of creating this novel computer architecture that led to the further development of novel and inventive data curation operations to feed the computer architecture for usable results. For example, the systems and method disclosed herein may identify a particular cohort of patients with medical records in a medical database, and curate the medical records for that cohort before providing the medical records to the computer architecture. Along with the innovative aspects of the computer architecture itself, these cohort identification and data curation operations, for practical application in the specific disclosed computer architectures, provide tools to identify clusters of patients with similar patient journeys, and to identify distinguishing medical events associated with different patient journeys.

Patient medical history data is often arranged as asynchronous, multi-level time-series data. For example, each patient may have an evaluation history, a testing history, a medication history, a diagnosis history, and/or other series or related time-separated medical events. Word-embedding techniques have been used to capture the relationship between events in different sequences. However, generic word-embedding techniques alone cannot be applied directly to medical records without generating disjointed or otherwise low quality output data. This is, at least in part, because medical events and medical histories do not possess linguistic structures of natural language data, and medical history data contain many levels of hierarchy that are deeper than those of human languages for which word-embedding techniques were developed.

Additionally, extracting static features out of the medical history data using conventional computing tools does not capture the chronological aspect of this medical data. For example, recommendation engines such as collaborative filtering engines require the data to be organized with individual patients in rows, and different medical events in columns, so that the algorithm can compute pair-wise similarities from the matrix. This type of data transformation, however, loses the chronological aspect that is critical for medical histories, and all events contribute equally for similarity computation regardless of when the event happened. And because medical decisions made by physicians and patients in the real world are based on sequential events, failure to capture the chronological, multi-level features of the medical data prevents generation of tools that would enhance the real-world applicability of medical records and other patient health data.

Conventional data science and statistical solutions involve converting time series data describing the occurrence discrete events along a patient journey into a static variable. It is impractical to create features that meaningfully captures the various and diverse comorbidity factors that relate to a particular disease(s) of interest in a patient journey. Due to the large number of potential comorbidity and risk factors and infinite variations in their time-dependent representation in the multi-dimensional medical data, processing and transformation of the multi-dimensional time-series data would result in an extremely large number of static variables. Having such a large number of static variables as the input data makes it technically challenging to converge machine learning solutions, which is classically known as the 'curse of dimensionality' problem in the artificial intelligence field. Furthermore, processing and transformation of time-series data into static variables rely on prior knowledge, imposing a selection bias and preventing the potential to discover new comorbidity factors and to understand the nuance in the relationship between confounding factors.

Thus, it would be useful to leverage longitudinal medical datasets (e.g., medical claims, EHR, and/or registry) in their entirety to identify different patient journey clusters, each representing a similar medical history, then investigating the distinguishing characteristics between clusters and clinical implications of the different disease progression sub-types, such as potential benefit of early biologic therapy in each patient journey cluster. By using the entirety of multi-dimensional time-series data, without static feature engineering, the relationships between different medical events are preserved for the machine learning analysis to create unbiased disease progression sub-types. Avoiding the need to transform time-series data into static features also increases scalability of the learning platform because prior knowledge specific to a particular disease is no longer necessary. For example, using the disclosed learning platform for the treatment of psoriasis patients, the application of the machine learning pipeline described below would help 1) delineate the subpopulation of psoriasis patients appropriate for early biologic treatment and 2) provide useful guidelines on clinical trial feasibility and establishment of inclusion and exclusion criteria for pharmaceutical R&D efforts, enhancing the clinical trial efficiency and success rate to bring promising products faster to the market and improving patient outcome. Furthermore, the clinical insights would be published to influence treatment guidelines from payors and healthcare providers Additionally, the output of the learning platform described in the embodiments disclosed herein may also be used to guide pharmaceutical research and development and commercial strategy development. For example, of the nearly 1 million psoriasis patients suffering annually in the United States with a moderate to severe disease, over 70% are not treated with an advanced biologic therapy. Of these patients, roughly 90 thousand will develop comorbid psoriatic arthritis in their lifetime. Since 70% of patients suffering from psoriatic arthritis struggle with psoriasis before experiencing any joint and soft tissue symptoms, it is very important to identify patients at risk for psoriatic arthritis before irreversible joint damage occurs, impairing the quality of life and physical function. In the dermatology and rheumatology medical fields, the use of biologic treatment to treat patients diagnosed only with psoriasis is generally believed to convey benefit in slowing or preventing the subsequent development of psoriatic arthritis. However, empiric evidence of a prophylactic benefit has not been established, and such investigation is not trivial to set up because psoriasis patients have numerous other comorbid indications (e.g., high blood pressure, other auto-immune diseases, and existing joint tissue conditions) in addition to their skin condition.

Accordingly, the present disclosure provides a mapping server having a medical-event embedding engine that is trained to operate on at least two time-separated medical events in medical records for a pre-identified cohort of patients. In some implementations, the medical-event embedding engine is provided with particular hyperparameters and hyperparameter values generated using information regarding the multi-level dimensionality of the medical records. The medical-event embedding engine is provided as part of a pipeline in an innovative computer architecture with a clustering engine that identifies clusters of patients in the cohort having similar patient journeys using the output of the medical-event mapping engine, and a cluster profiling engine that identifies distinguishing medical events for each of the clusters using the output of the clustering engine.

The disclosed system provides a technical solution (e.g., using medical-event embedding, clustering, and profiling engines) to the technical problem generating actionable displays of information representing vast amounts of electronic medical data.

Although many examples provided herein describe the use of patient medical records, each patient may grant explicit permission for anonymized aspects of medical information to be stored and/or analyzed in accordance with HIPAA (Health Insurance Portability and Accountability Act of 1996) and all other state and local requirements that ensure data privacy and security provisions for safeguarding medical information. The explicit permission may be granted prior to storage of medical records and/or using privacy controls integrated into the disclosed system. Each patient may be provided notice that such patient information will be stored and/or analyzed with explicit consent, and each patient may, at any time, end having the information stored and/or analyzed, and may delete any stored patient information. The stored patient information may be encrypted to protect patient security.

The patient can, at any time, delete the patient information from memory and/or opt out of having the patient information stored in memory. Additionally, the patient can, at any time, adjust appropriate privacy settings to selectively limit the types of patient information stored in memory, or select the memory in which the patient information is stored (e.g., in a particular medical database as opposed to remotely on a server). The patient information does not include and/or share the specific identification of the patient (e.g., the patient's name) unless directed and authorized by the patient.

Example System Architecture

FIG. 1 illustrates an example architecture 100 for machine learning for patient journey mapping, suitable for practicing some implementations of the disclosure. The architecture 100 includes mapping server 130, medical records database 120, and user devices 110 connected over a network 150. As shown, various medical information systems may also be communicatively coupled to mapping server 130, medical records database 120, and/or user devices 110 via network 150. These medical information systems may include hospital system 102, pharmacy systems 104, laboratory system 106, provider systems 108, and/or any other systems that generate and/or store medical event information for patients.

Hospital systems 102, pharmacy systems 104, laboratory systems 106, and/or provider systems 108 such as medical office systems, physician systems, or urgent care systems may store information associated with medical events for various patients. The medical events may include test administrations, test results (e.g., physical or mental performance exam results, practitioner evaluation results, etc.), diagnoses, laboratory results (e.g., blood work results, urinalysis results, x-rays, imaging and/or tomography scans, genetic test results, etc.), prescriptions, medication schedules, surgeries, and the like. Each of hospital systems 102, pharmacy systems 104, laboratory systems 106, provider systems 108, and/or other medical information systems may store medical event information for medical events that occurred at an associated medical facility.

In some scenarios, medical event information from each of hospital systems 102, pharmacy systems 104, laboratory systems 106, provider systems 108, and/or other medical information systems can be provided to a central medical records database such as medical records database 120. Medical records database 120 may be a database that is associated with mapping server 130 or may be a third-party database. One example of such a third-party medical records database is the Optum® electronic health records (EHR) database of Optum, Inc. of Eden Prairie, MN.

One or more mapping servers, such as mapping server 130, may be communicatively coupled to medical records database 120 for obtaining medical records for a particular cohort of patients that have medical records in the medical records database. Mapping server 130 may provide an interface that facilitates interactive review of the medical records in the database to pre-identify a cohort of patients for patient journey mapping, by mapping server 130.

User devices 110 may be used by patients, providers, and/or operators of mapping server 130 for various communications with medical records database 120, mapping server 130, hospital system 102, pharmacy systems 104, laboratory systems 106, and provider systems 108. For example, patients may use a user device 110 to access or update their own medical records at any of medical records database 120, mapping server 130, hospital systems 102, pharmacy systems 104, laboratory systems 106, and provider systems 108. An operator of mapping server 130 may use a user device 110 as an interface with mapping server 130, though it should be appreciated that mapping server 130 may also include its own interface components. Outputs from mapping server 130 may be displayed on a display associated with the mapping server, or may be provided (e.g., via network 150) for display on another device such as one or more of user devices 110, hospital systems 102, pharmacy systems 104, laboratory systems 106, or provider systems 108.

One or more mapping servers 130 is configured to host machine-learning and other statistical analysis engines, such as a machine-learning engine implementing a computer-operated neural network. The neural network includes parameters trained such that the neural network forms a medical-event embedding engine trained to generate an output vector corresponding to a medical event in an input medical record. Training the neural network allows the neural network to learn the association of a target medical event with neighboring medical events. The spatial representations of the medical events reflect the meaning and relationship between different medical events.

However, because medical events are multi-dimensional over time, it was discovered that it is not practical to use neural network hyperparameters that are typically associated with creating word-embedding engines for natural language recognition because those parameters are tuned by using a natural language data with its intrinsic linguistic structure. An electronic medical record, however, includes multiple occurrences of a series of time variant events, each series with its own structure that does not resemble a natural language structure. For example, a first series may be a diagnosis history where a physician may note one or two diagnosis codes in the patient record while ordering a dozen different lab tests at the same time. Meanwhile, in a second series describing medication history, the patient may be treated with different medications in their own individual cadences. Accordingly, the medical records for the patient include multidimensional overlapping or concurrent timelines of medical events. Because of these unique characteristics of medical records, particular sets of hyperparameters are generated to provide uniquely architected neural networks to create medical-event embedding engines useful for analysis of particular diseases. Various combinations of unique hyperparameters, including (for example) the window size, vector dimension, and negative sampling rate are selected for each disease to tune the medical-event embedding for that disease.

Accordingly, and as described in further detail herein, one or more medical-event embedding engines are provided within a mapping server 130, each characterized by a unique structure as provided by the unique set of hyperparameters, and each having a trained set of parameters as described in further detail hereinafter.

Medical records from the medical records database, and known patient journey information for known disease progressions can be used to train the medical-event embedding engine to generate numerical vectors representing individual medical events.

Mapping server 130 includes a processor, memory, and communications capability for hosting the medical-event embedding engine and other modules described herein. User devices 110 can be, for example, desktop computers, mobile computers, tablet computers (e.g., including e-book readers), mobile devices (e.g., a smartphone or a PDA), or any other devices having appropriate processor, memory, and communications capabilities for accessing other systems and devices via network 150. The network 150 can include, for example, any one or more of a local area network (LAN), a wide area network (WAN), the Internet, and the like. Further, the network 150 can include, but is not limited to, any one or more of the following network topologies, including a bus network, a star network, a ring network, a mesh network, a star-bus network, a tree or hierarchical network, and the like.

Example Mapping Server

Figure 2:
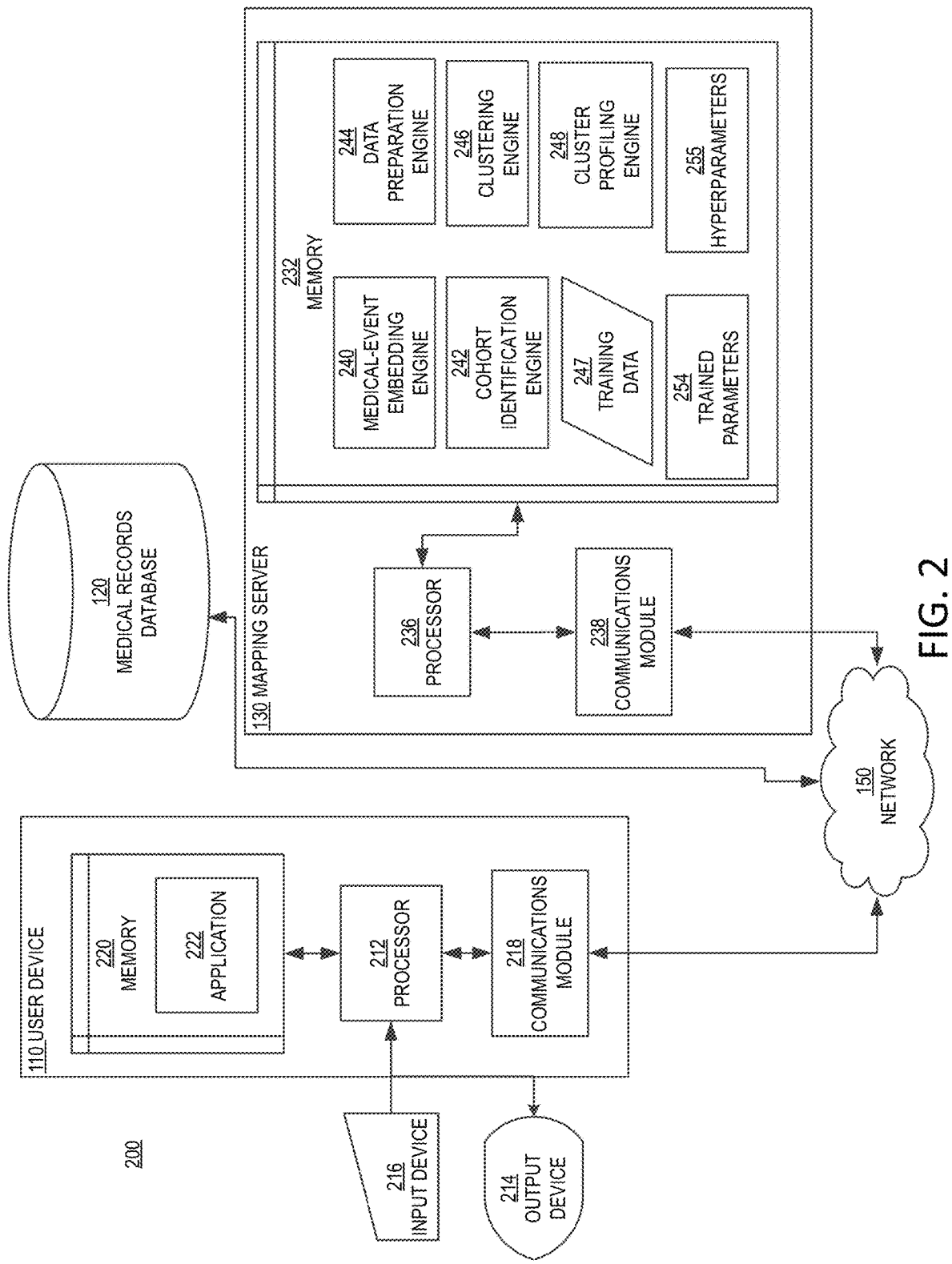
FIG. 2 is a block diagram illustrating an example user device, mapping server, and medical records database from the architecture of FIG. 1, according to certain aspects of the disclosure.

FIG. 2 is a block diagram 200 illustrating an example mapping server 130, medical records database 120, and user device 110 in the architecture 100 of FIG. 1, according to certain aspects of the disclosure. The user device 110, mapping server 130, and medical records database 120 are connected over the network 150 via communications modules 218 and 238. The communications modules 218 and 238 are configured to interface with the network 150 to send and receive information, such as data, requests, responses, and commands to other devices on the network. The communications modules 218 and 238 can be, for example, modems or Ethernet cards.

As shown, user device 110 may include a memory 220 storing an application 222 such as an interface application for interfacing with mapping server 130 via communications module 218. User device 110 may include one or more input devices such as input device 216 (e.g., a mouse, a keyboard, a touchscreen, a microphone, or the like) and one or more output devices such as output device 214 (e.g., a display, a speaker, or the like).

The mapping server 130 includes a memory 232, a processor 236, and a communications module 238. The memory 232 of the mapping server 130 includes a medical-event embedding engine 240, a cohort identification engine 242, a data preparation engine 244, a clustering engine 246, and a cluster profiling engine 248. As indicated in FIG. 2, memory 232 may store trained parameters 254 (for one or more of medical-event embedding engine 240, cohort identification engine 242, data preparation engine 244, clustering engine 246, and cluster profiling engine 248), and hyperparameters 255 for medical-event embedding engine 240. In one or more implementations, each of medical-event embedding engine 240, clustering engine 246, and cluster profiling engine 248 may include a machine-learning model that implements a neural network.

For example, the machine-learning model may utilize a deep neural network architecture or other deep-learning architecture. The medical-event embedding engine 240 may be provided with medical events such as two or more time-separated medical events in the medical records in medical records database 120 for a cohort of patients. The cohort of patients may be pre-identified by cohort identification engine 242, prior to extraction of the medical records for the cohort from medical records database 120. In some scenarios, data preparation engine 244 may modify the medical records for the pre-identified cohort, before the medical events of the medical records are provided to medical-event embedding engine 240.

The medical-event embedding engine 240 may be trained to generate vector representations of medical events in a continuous vector space, using training data 247 stored in memory 232 and/or medical records data from medical records database 120. The medical-event embedding engine 240 may employ any one of multiple word embedding techniques to generate a numerical representation of medical events for processing by a computational device. Exemplary word embedding techniques may include Word2Vec and FastText. Once vectors associated with medical events have been generated by medical-event embedding engine 240, the vectors may be combined (e.g., within the medical-event embedding engine 240 and/or using processor 236) to form single vector representations of the patient histories of each patient in the pre-identified cohort. Clustering engine 246 operates on the single vector representations of the patient medical histories to identify clusters of the patients in the pre-identified cohort that have similar patient journeys.

Once the clusters of patients have been identified, and a cluster label is generated by clustering engine 246 for each cluster of patients, cluster profiling engine 248 operates on the single vector representations to identify distinguishing medical events for each cluster.

In the following discussion, further details of patient journeys, as described herein, are discussed in connection with FIG. 3, further details of the pipeline generated by medical-event embedding engine 240, cohort identification engine 242, data preparation engine 244, clustering engine 246, and cluster profiling engine 248 are discussed in connection with FIG. 4, and an example output in which at least relative numbers of the distinguishing medical events for various clusters of patients are provided for display are discussed in connection with FIG. 5.

However, returning for now to FIG. 2, it should be appreciated that, in order to train medical-event embedding engine 240, input training data such as input medical events from medical records database 120 and associated with a disease with known associations between those medical events in the disease progression, and output training data such as previously generated vectors representing the known associations, may be provided to, for example, a neural network architecture or other machine-learning architecture for training the neural network to produce a machine-learning model for medical-event embedding engine 240 (e.g., by tuning parameters such as weights between neurons of the network, biases, thresholds, and/or other aspects of the model). In this way, the machine-learning engine may be trained so that medical events, associated with diseases having unknown progressions or a wide spectrum of clinical manifestations, that are provided to the machine-learning model cause the medical-event embedding engine 240 to generate embedded medical history data such as vectors in the continuous vector space for each of several medical events.

The disclosed arrangement of mapping server 130, in which the medical histories of patients in a pre-identified cohort are embedded in single vector representations, and the single vector representations are clustered and profiled to identify distinguishing medical events for each of several clusters of the patients, provides a technical solution to the technical problem of processing large, multi-dimensional, time-series datasets, and provides various improvements to the functioning of the computer, including by providing an arrangement that allows the capability of parallel processing within one or more of the engines in memory 232, and among the various engines of memory 232.

The processor 236 of the mapping server 130 is configured to execute instructions, such as instructions physically coded into the processor 236, instructions received from software in memory 232, or a combination of both. For example, the processor 236 of the mapping server 130 executes instructions to operate cohort identification engine 242 to identify a cohort of patients having at least one common medical event in the medical records of each of the patients, and each medical record including at least two time-separated medical events; to operate medical-event embedding engine 240 on the at least two time-separated medical events to generate embedded medical history data (e.g., vectors corresponding to medical events, and single vector representations of entire patient medical histories) for the pre-identified cohort of patients; to operate clustering engine 246 on the embedded medical history data to identify at least one cluster of the patients in the pre-identified cohort that have similar patient journeys; to operate cluster profiling engine 248 on the embedded medical history data of the patients in the at least one cluster to identify differentiating medical events of the at least one cluster of the patients in the pre-identified cohort that have similar patient journeys; and/or to provide, for display, at least relative numbers of the differentiating medical events of the at least one cluster of the patients in the pre-identified cohort that have similar patient journeys. The processor 236 may be processing device that includes a large number of cores and a suitable memory architecture designed for processing a very large number of calculations on many hundreds or thousands of parameters included in a data set, such as a medical records database 120 described herein, using multiple parallel processes. For example, the processor 236 may be a specialized processor, such a purpose-built neural network processor or a graphics processing unit (GPU). Neural network model training, such as training performed by medical-event embedding engine 240, involves matrix math calculations, which can be processed more quickly in parallel. GPUs are designed to compute multiple but simpler calculations in parallel, compared to conventional central processing units.

Figure 3:
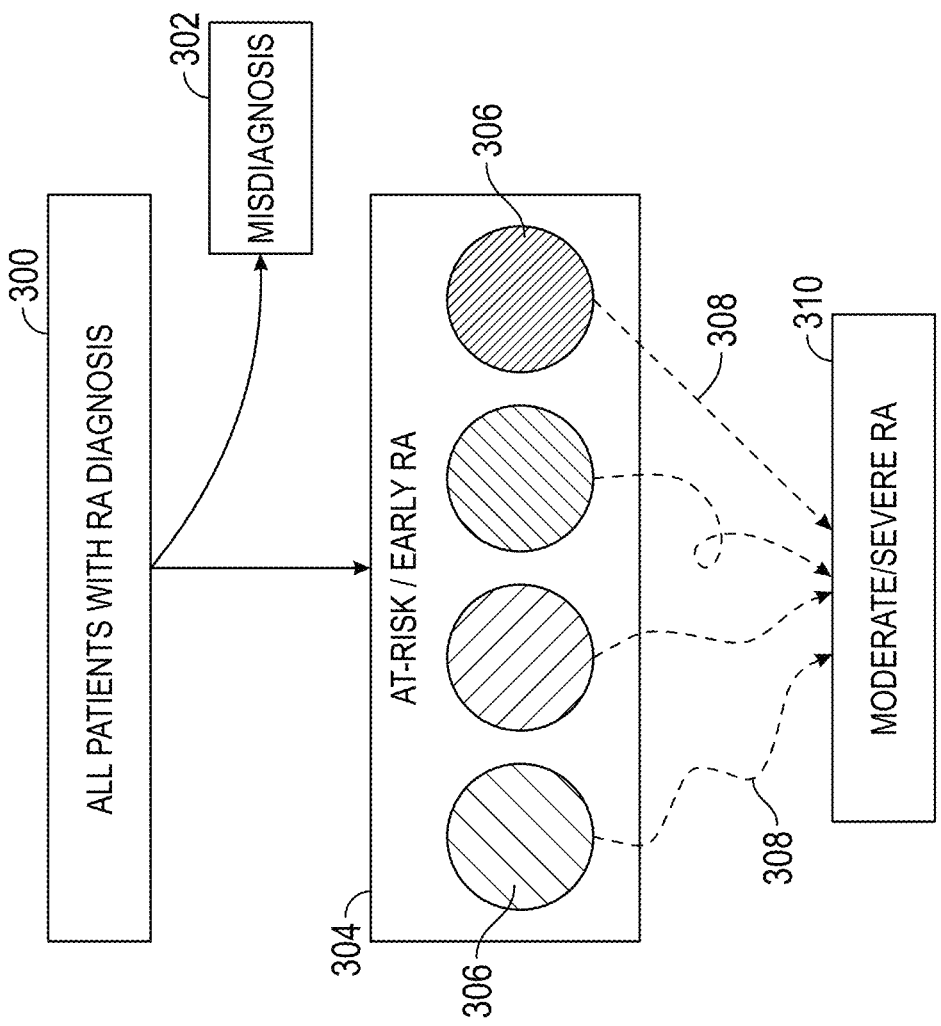
FIG. 3 illustrates example patient journeys, according to certain aspects of the disclosure.

FIG. 3 is a schematic diagram illustrating various patient journeys, in one particular example of patients having been diagnosed with rheumatoid arthritis (RA). It should be appreciated that, although the discussion of FIG. 3 and other figures such as FIGS. 4, 5, 7, and 8 utilize this example of RA, the systems and methods disclosed herein (e.g., with appropriate adjustments to machine-learning training and model hyperparameters) can be applied to other diseases such as various auto-immune diseases, cancers, neurological diseases, or the like.

As illustrated in FIG. 3, a cohort 304 of patients 306 that are at risk of, or are in the early stages of RA, may be identified out of a larger subset 300 of patients with any RA diagnosis (e.g., by excluding patients 302 in the larger subset 300 having been misdiagnosed, which may be determined by another, subsequent, conflicting, or overriding diagnosis in the patients' medical record or based on other exclusion criteria such as lab tests or procedures that indicate a different diagnosis). However, as indicated, the patients 306 in the identified cohort 304 may follow different patient journeys 308 from the at-risk/early stage to the moderate/severe RA stage 310.

These different patient journeys 308 may be differentiated by particular medical events along that particular journey, such as treatments with particular medications (e.g., prednisone or leflunomide in the example of RA), treatments with biologic therapies, identifications of family history indications, or onset of hypothyroidism.

Figure 4:
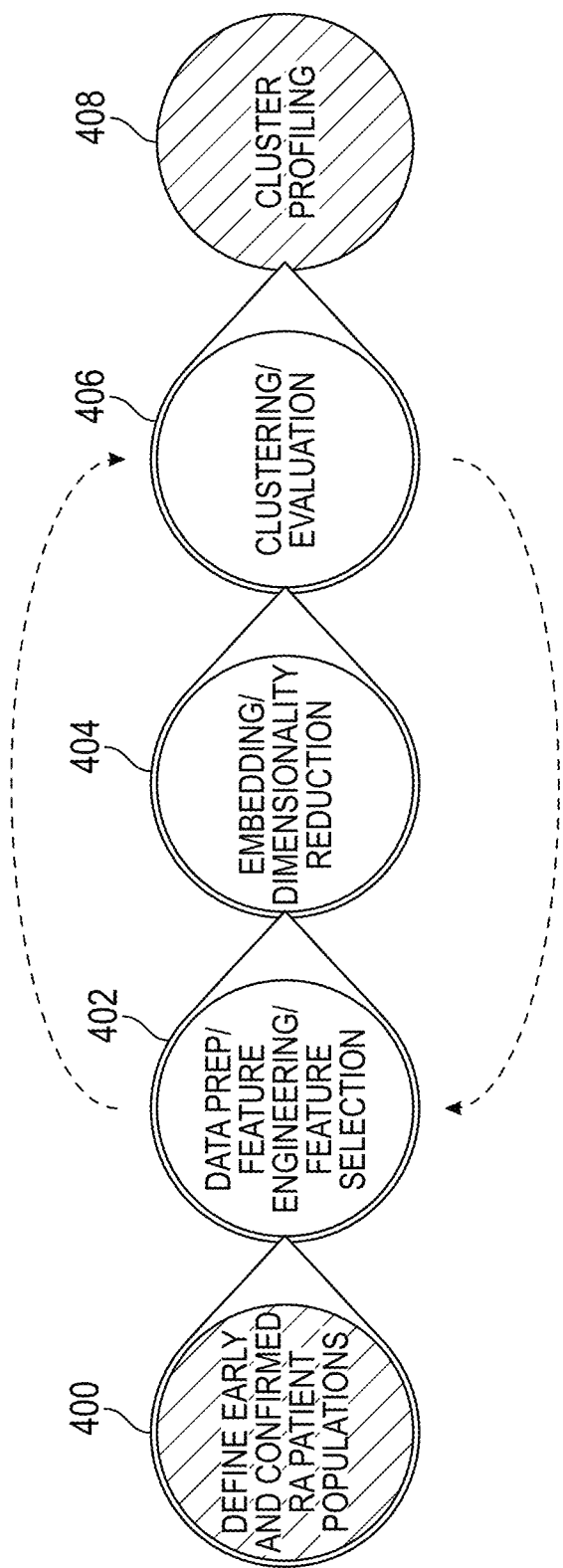
FIG. 4 illustrates an example flow diagram for machine-learning based patient journey mapping, according to certain aspects of the disclosure.

FIG. 4 illustrates a pipeline of operations that may be performed by mapping server 130 to identify and distinguish clusters of patients 306 in cohort 304 that have similar patient journeys 308. As shown in FIG. 4, mapping server 130 (e.g., by operation of cohort identification engine 242) may perform a cohort identification operation 400 that defines the cohort 304 of patients 306 having early and confirmed RA diagnoses. Mapping server 130 (e.g., by operation of data preparation engine 244) may perform a data preparation/feature engineering/feature selection operation 402, prior to providing the medical record for each of the patients in the cohort to medical-event embedding engine 240 that modifies the medical records of the patients in the cohort by mapping a set of codes in the medical records to a set of generic identifiers, removing duplicate medical events in predetermined time period (e.g., in a single day, week, month, or other time period) from the medical records, and/or randomizing an order of medical events in the predetermined time period.

Mapping server 130 may then (e.g., by operation of medical-event embedding engine 240) perform a medical-event embedding operation 404 to generate vectors associated with medical events in the medical records, and to generate single vector representations of the patient medical histories using the generated vectors. In some operational scenarios, mapping server 130 may perform one or more dimensionality reduction operations on the single vector representations. For example, non-linear dimensionality reduction operations (e.g., spectrum embedding and auto-encoding operations) may be performed on the single vector representations to reduce the dimensionality of the single vector representations from hundreds of dimensions to a few dimensions.

Mapping server 130 may then (e.g., by operation of clustering engine 246 on the single vector representations) perform a clustering operation 406 to identify one or more clusters of the patients 306 in the cohort 304 that have similar patient journeys 308. While the dimensionality reduction operation helps with reducing the overall computational complexity of the clustering operation, it was discovered that in many cases it can be difficult or impossible to fit the entire patient dataset into a single computational run, due to the number of patients in the dataset. To overcome this problem, two different solutions were engineered: In the first solution, the clustering operation 406 can include selecting a subset (e.g., one third or another fraction) of the patient cohort 304 and generating (e.g., with clustering engine 246) clusters and associated cluster labels for the subset. In order to propagate the cluster labels to the rest of the patients in the cohort, clustering engine 246 operates again on the single vector representations (prior to the dimensionality reduction step) for the other patients in the cohort but using the known cluster labels, and iteratively and populates the cluster labels for the subset, using the existing labels to enlarge the clusters (e.g., by assigning more of the patients in the cohort to that cluster) in an iterative manner. In this way, the cluster labels can be generated, without supervision, for the cohort, while still allowing processing of large sets of patient data. As indicated by the dashed arrows in FIG. 4, mapping server 130 may iteratively cycle through operations 402, 404, and 406 to further define the clusters as desired. In the second solution, a neural-network based dimensionality reduction method is employed so that batches/chunks of the patient dataset could be fed into the server over a set number of iterations. This solution allows the dimensionality reduction and subsequent clustering operation of the entire dataset, without having to propagate the cluster labels and enlarge clusters.

Mapping server 130 may then (e.g., by operation of cluster profiling engine 248 on the single vector representations, the medical-event vectors from clustering engine 246, and/or the medical records themselves) perform a cluster profiling operation 408 that identifies differentiating medical events for each identified cluster. Identification of these differentiating medical events allows mapping server 130 to generating information, for display, that illustrates why a cluster of patient medical histories is distinct from other clusters.

The cluster profiling operation may include determining, for each medical event for each of the patients in the cohort, the number of occurrences in a given cluster, normalized by the total number medical events in the cluster (e.g., in order to adjust for the varying lengths of medical histories from cluster to cluster). The computed frequencies of each medical event (e.g., the term frequency, TF) can be obtained from the inverse of the weighted numbers of the events to represent the weight or the importance of the medical events in the cluster.

These frequencies may then be further adjusted by multiplying each frequency with the inverse frequencies of the same medical event in other clusters (e.g., inverse cluster frequency, ICF). In this way, the inverse frequencies are applied to penalize a medical event that appears in most or all of the clusters. For example, in the example of FIG. 3, a diagnosis of RA is a medical event that is guaranteed to happen for every patient, due to the design of the patient cohort. Thus, the RA diagnosis event would have a relatively high TF. However, since all patients in the cohort have this diagnosis, the ICF of the RA diagnosis event would be very low. Consequently, the product of TF and ICF would be small for all clusters, indicating that this event is not specific to any particular cluster and is thus not a distinguishing medical event for any cluster.

Following the operations of FIG. 4, mapping server 130 may provide, for display, at least relative numbers of the distinguishing medical events for one or more of the clusters. FIG. 5 illustrates an example in which the relative numbers of the distinguishing medical events are provided in a graphical display for five clusters and six distinguishing medical events. In the example of FIG. 5, a graphical representation is provided that indicates the relative numbers of patients in each of Cluster 1, Cluster 2, Cluster 3, Cluster 4, and Cluster 5 (each having been identified by clustering engine 246) having been treated with prednisone, having been treated with leflunomide, having hypothyroidism, having received biologic therapy, and having received biologic therapy within five years of diagnosis.

Figure 5:
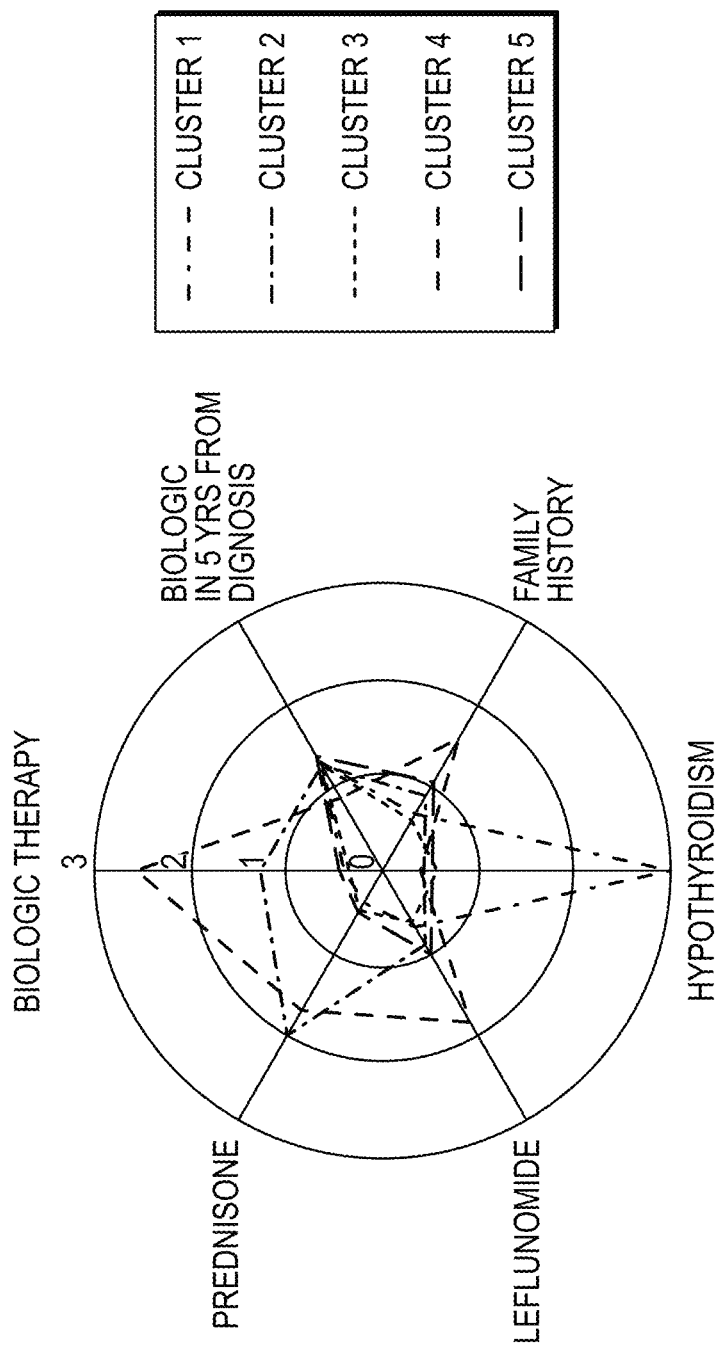
FIG. 5 illustrates an example output of a machine-learning based patient journey mapping operation, according to certain aspects of the disclosure.

As can be seen in FIG. 5, in this example of RA, Cluster 4 shows a correlation between the distinguishing medical events of biologic therapy, leflunomide treatment, and family history, without any correlation with hypothyroidism. However, Cluster 1 shows a common occurrence of hypothyroidism, and Clusters 3 and 5 show almost no treatment with biologic therapy.

It should be appreciated that cluster profiling engine 248 identifies the distinguishing features of each cluster, after the clusters are identified, rather than the clusters being forced to conform to pre-determined cluster labels.

Figure 6:
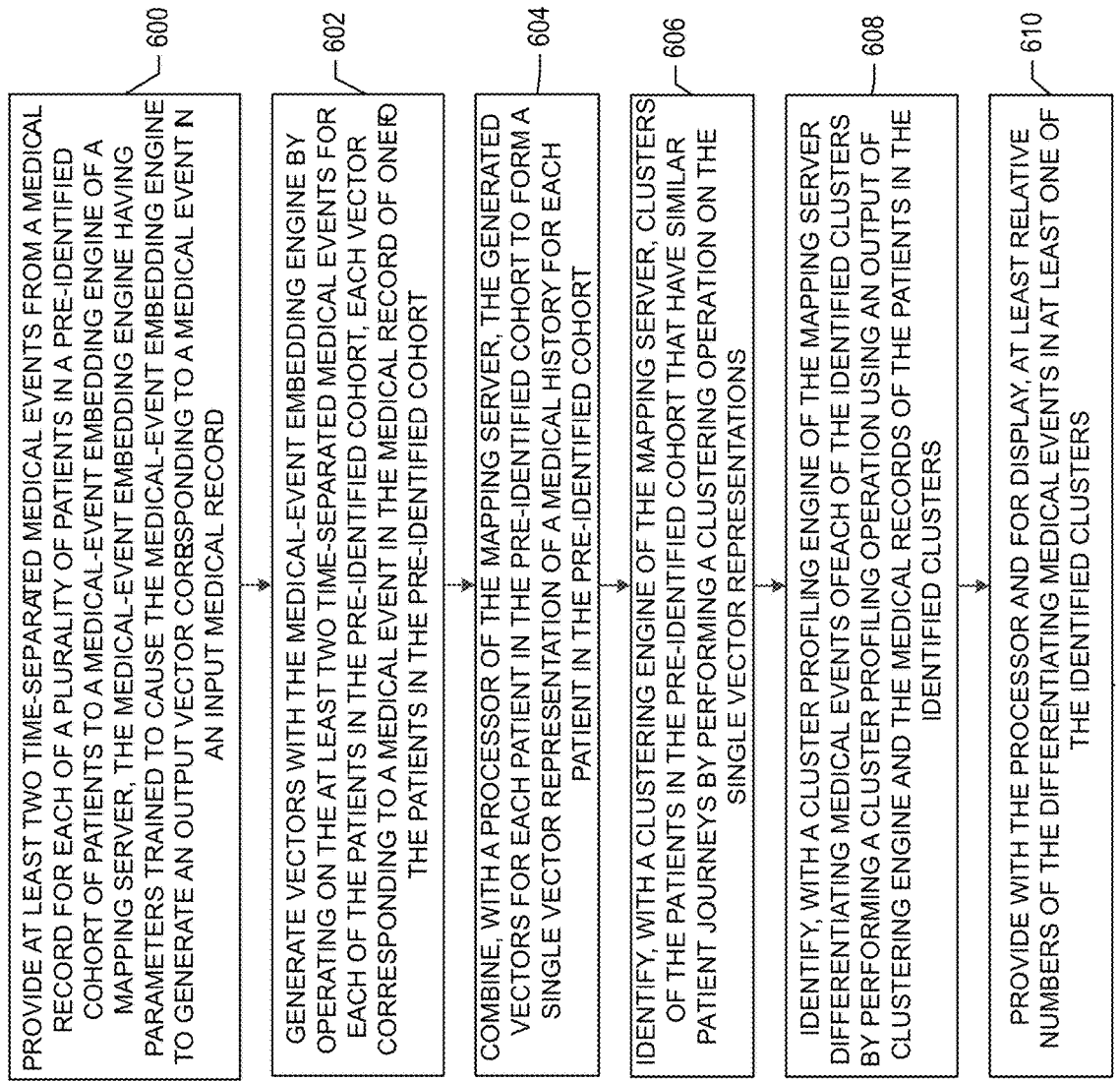
FIG. 6 illustrates an example process for machine-learning based patient journey mapping, according to certain aspects of the disclosure.

FIG. 6 illustrates a flow diagram of an example process for patient journey mapping using machine learning, in accordance with one or more implementations. For explanatory purposes, the process of FIG. 6 is primarily described herein with reference to one or more devices of FIGS. 1 and 2 (particularly with reference to mapping server 130), which may be executed by one or more processors of the mapping server 130 of FIGS. 1 and 2. However, the process of FIG. 6 is not limited to the server 130, and one or more blocks (or operations) of the process may be performed by one or more other components of other suitable devices. Further, for explanatory purposes, the blocks of the process of FIG. 6 are described herein as occurring in serial, or linearly. However, multiple blocks of the process of FIG. 6 may occur in parallel. In addition, the blocks of the process of FIG. 6 need not be performed in the order shown, and/or one or more blocks of the process of FIG. 6 need not be performed and/or can be replaced by other operations.

At block 600, at least two time-separated medical events are provided from a medical record for each of a plurality of patients (e.g., patients 306 of FIG. 3) in a pre-identified cohort (e.g., cohort 304) of patients to a medical-event embedding engine (e.g., medical-event embedding engine 240) of a mapping server (e.g., mapping server 130), the medical-event embedding engine having parameters (e.g., parameters 254) trained to cause the medical-event embedding engine to generate an output vector corresponding to a medical event in an input medical record.

At block 602, the medical-event embedding engine 240 generates vectors by operating on the at least two time-separated medical events for each of the patients in the pre-identified cohort, each vector corresponding to a medical event in the medical record of one of the patients in the pre-identified cohort.

In some operational scenarios, the medical records may be modified before the medical records are provided to the medical-event embedding engine. Modifying the medical records may include curating the medical records for the pre-identified cohort by, for example, mapping a set of codes in the medical records to a set of generic identifiers. For example, for the cohort patients, the medical records can be compiled in chronological order from the medical records database. Although the sequence of medical events can be directly fed into medical-event embedding engine 240, medical data from the real world pose unique challenges for producing usable embedding results. For example, the medical events in the medical records may have many levels of hierarchy that are deeper than in, for example, human languages. For example, the hierarchy in medical codes varies from one type of code to another and may not be consistent between different versions. In one example, the International Classification of Diseases changed its code structure significantly from version 9 to 10. The depth and variety in medical event codes is one reason why there are many codes that are very rarely found in the data. To overcome this challenge, drug codes in the medical database (e.g., National Drug Codes provided by Optum®) can be mapped to generic product identifiers (e.g., Generic Product Identifiers (GPIs) from Medi-Span®). Converting the medical codes in the medical records to GPIs can reduce the number of unique medication terms to approximately 13,000 from approximately 30,000. Use of GPIs can also be advantageous in that the GPI structure is based on the mechanism of action of the medication, allowing for further reduction of unique medication terms by rolling up the terms in its hierarchy.

For example, a second characteristic of medical data that is different from normal text data is that several medical events often happen at the same time (e.g., a physician may prescribe several medications at once, or two different physicians may give the same diagnosis in a single day). To account for these duplications and simultaneous events, modifying the medical records may also include curating the medical records, removing duplicate medical events in a predefined time period (e.g., a single day, a week, a month, etc.) from the medical records, and/or randomizing an order of medical events in the predefined time period.

It should also be appreciated that medical-event embedding engine 240 can operate on two, three, four, more than four, tens, hundreds, thousands, or millions of medical events in various multidimensional timelines for any desired number of patients.

At block 604, mapping server 130 (within medical-event embedding engine 240 or separately therefrom) combines the generated vectors for each patient in the pre-identified cohort to form a single vector representation of a medical history for each patient in the pre-identified cohort. In this way, the sequence of events in multiple layers of the medical records can be incorporated into identifying clusters of patients and/or similar patient journeys in subsequent operations. Exemplary operations that may be performed for combining the generated vectors are discussed hereinafter in connection with, for example, FIG. 9.

In some operational scenarios, mapping server 130 reduces the number of dimensions of the single vector representations prior to the clustering operation. The number of dimensions can be reduced by operating on the single vector representations in a spectrum-embedding operation, a principle component analysis operation, or another dimensionality reduction operation.

At block 606, a clustering engine, such as clustering engine 246 of FIG. 2 of the mapping server, identifies clusters of the patients in the pre-identified cohort that have similar patient journeys by performing a clustering operation on the single vector representations. Exemplary operations that may be performed for identifying clusters are discussed hereinafter in connection with, for example, FIG. 10.

At block 608, a cluster profiling engine such as cluster profiling engine 248 of FIG. 2 of the mapping server identifies differentiating medical events (see, e.g., the differentiating medical events described in connection with FIG. 5 as an example) of each of the identified clusters by performing a cluster profiling operation using an output of the clustering engine (e.g., the cluster labels and/or identifiers of the patients in each cluster) and the medical records of the patients in the identified clusters (e.g., the raw medical records, the modified medical records, and/or embedded medical history data based on the medical records). Exemplary operations that may be performed for identifying differentiating medical events are discussed hereinafter in connection with, for example, FIG. 11.

At block 610, the mapping server 130 provides, with the processor 236 and for display (e.g., with the mapping server or a user device 110), at least relative numbers of the differentiating medical events in at least one of the identified clusters. The at least relative numbers of the differentiating medical events can be provided in graphical representation of one or more clusters as in the graphical representation of FIG. 5, or in other representations such as in charts or tables of relative or absolute numbers of the differentiating medical events in each cluster.

Figure 7:
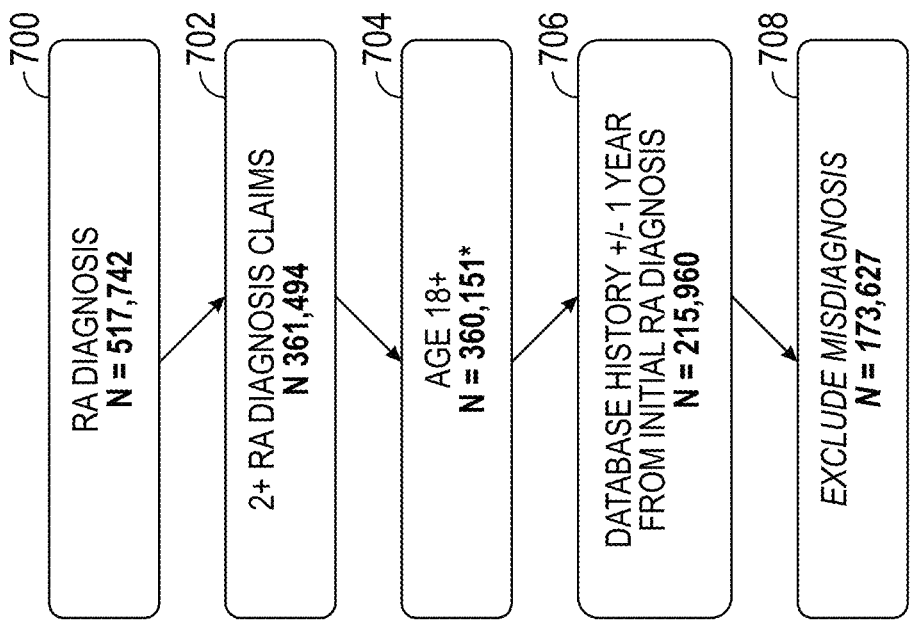
FIG. 7 illustrates an example process for cohort identification, according to certain aspects of the disclosure.
Figure 8:
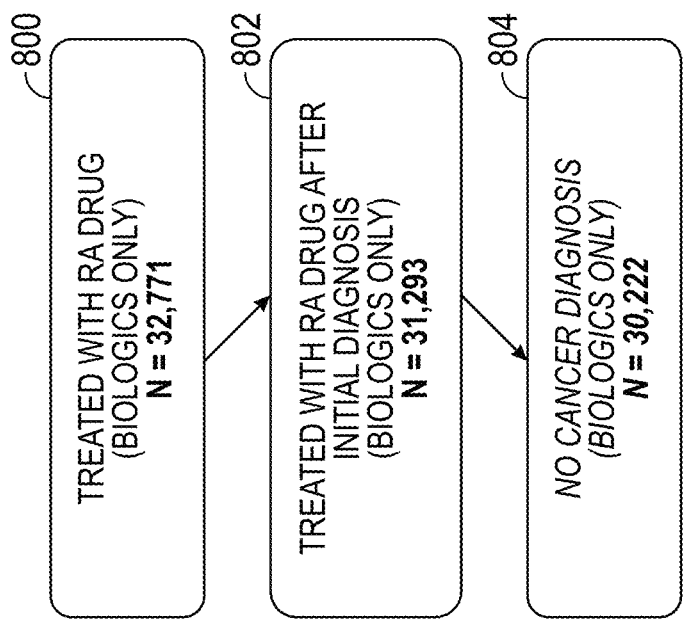
FIG. 8 illustrates another example process for cohort identification, according to certain aspects of the disclosure.

FIGS. 7 and 8 show two respective examples of cohort identification operations 400 that may be performed by cohort identification engine 242 of mapping server 130. In the example of FIG. 7, at block 700, a first subset of the patients with medical records in medical records database 120 is identified. At block 700, the first set of patients having a common diagnosis of RA is identified with, for example, 517,742 patients.

At block 702, to curate the patient cohort, a second subset of the first subset with at least two diagnosis claims of rheumatoid arthritis (RA) in a particular time period (e.g., a span of several years) can be identified.

At block 704, a third subset of the second subset can be identified, the third subset having a particular age range (e.g., 18 years or older) at the first diagnosis of RA.

At block 706, a fourth subset of the third subset can be identified to identify the cohort, the fourth subset having medical events within a medical history range of at least one year before and one year after the initial diagnosis of RA.

At block 708, a fifth subset of the fourth subset can be identified to identify the cohort, by excluding patients with a misdiagnosis of RA (e.g., patients that had a related auto-immune disease diagnosis after getting the first diagnosis of RA). In the example of FIG. 7, a final cohort (e.g., with ~170,000 patients) representing a population of RA patients is identified.

In the example of FIG. 8, another example of cohort identification for the example of RA patients is provided in which, at block 800, a first subset of patients with at least two time-separated events in the medical records, and that have been treated with biologics for RA is identified.

At block 802, a second subset of the first subset is identified for which the biologics were provided after the initial RA diagnosis.

At block 804, a third subset of the second subset is identified to identify the cohort by excluding patients with a cancer diagnosis.

It should be appreciated that the examples of FIGS. 7 and 8 are specific to the example of RA diagnoses. However, in general, identifying the cohort may include identifying a set of patients with a common medical event in the medical records; reducing the set of patients based on a sequence of events in the medical records; and further reducing the set of patients by excluding patients based on a diagnosis in the medical records. Excluding the misdiagnosed patients may include identifying an additional diagnosis of a different condition subsequently to the diagnosis with the particular condition, or ruling out the initial diagnosis based on procedures, lab tests, or other medical events in the medical records. In the example of FIG. 7, the common medical event includes a first diagnosis (e.g., an RA diagnosis) in the medical records, the diagnosis in the medical records is a second diagnosis different from the first diagnosis, and the sequence of events is a sequence of events spanning at least one year before and one year after the first diagnosis. In the example of FIG. 8, the common medical event includes a treatment with a drug (e.g., biologics), and the sequence of events includes treatment with the drug after a diagnosis (e.g., treatment with the biologics after an initial diagnosis).

The operations of medical-event embedding engine 240 provides vector representations of individual medical events. Because each patient medical history includes one or more sequences of these events, an additional vector combination operation is performed as described above in connection with block 604 of FIG. 6 to represent an entire medical history as a vector, rather than a sequence of vectors.

This vector combination operation can include computing an average (e.g., a centroid) of all vectors representing medical events from a patient journey for a particular patient. The average vector is a single vector representation of the patient's entire medical history that can be used to find patients who have gone through the similar medical journeys.

Figure 9:
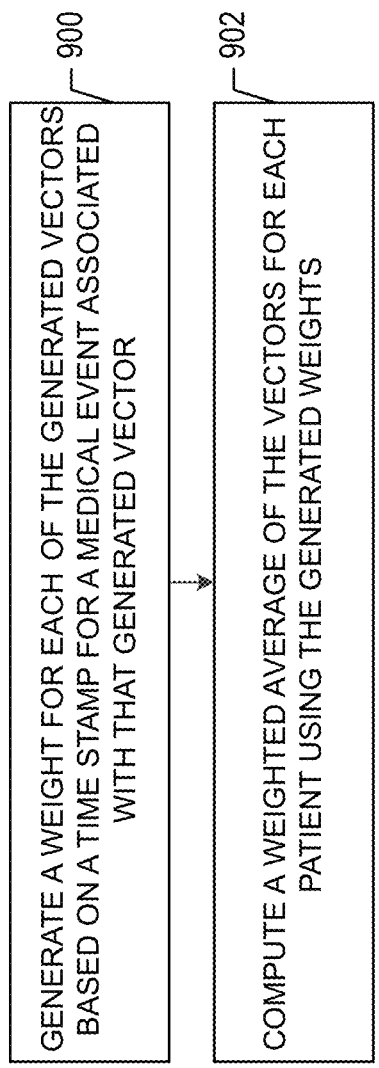
FIG. 9 illustrates an example process for combining vectors from a medical-event embedding engine to form single vector representations of patient histories, according to certain aspects of the disclosure.

FIG. 9 is a flow chart of illustrative operations that can be performed for combining the generated vectors from medical-event embedding engine 240. At block 900, the processor of mapping server 130 generates a weight for each of the generated vectors (e.g., using a time stamp for the medical event corresponding to that generated vector, a medical history prior for the patient corresponding to that generated vector, or other weighting factors).

At block 902, a weighted average of the generated vectors for each patient is computed by applying (e.g., multiplying) the weights to each vector and summing the weighted vectors. In the example in which time-stamp based weights are used, more recent past events (e.g., having vectors with more recent time stamps) are caused to have a bigger influence on the present and future events and decisions than vectors with older time stamps, by applying time-stamp based weights to calculate the average of all events from a single patient. In addition to the time-based weights, weights may be generated based on prior medical knowledge or other weighting factors, and one or more different weights can be applied simultaneously to each vector.

Although the example of FIG. 9 generates a weighted average of the generated vectors to combine the vectors into a single vector representation, in other implementations, it is possible to train a supervised model and take the learned representations for clustering. However, to train a supervised algorithm, one must decide first what the dependent variable is going to be, and many times it is difficult to assign a clear dependent variable because the goal of patient journey mapping is to generate the hypothesis variables based on the analysis itself. Accordingly, in many circumstances, an unsupervised medical-event embedding operation and weighted average vector combination may be preferable.

As described above in connection with block 606 of FIG. 6, once the single vector representations of the patient medical histories have been generated, clustering engine 246 can operate on the single vector representations to identify clusters of patients in the cohort that have similar patient journeys (see, e.g., patient journeys 308 of FIG. 3).

Clustering in very large dimensions often does not provide meaningful clusters because of the well-known "hubness problem." While the dimensionality reduction operations described above can help with reducing the overall computational complexity, it can still be difficult or impossible to fit the entire patient data for a useful cohort into a single computational run, due to the number of patients in the cohort.

Figure 10:
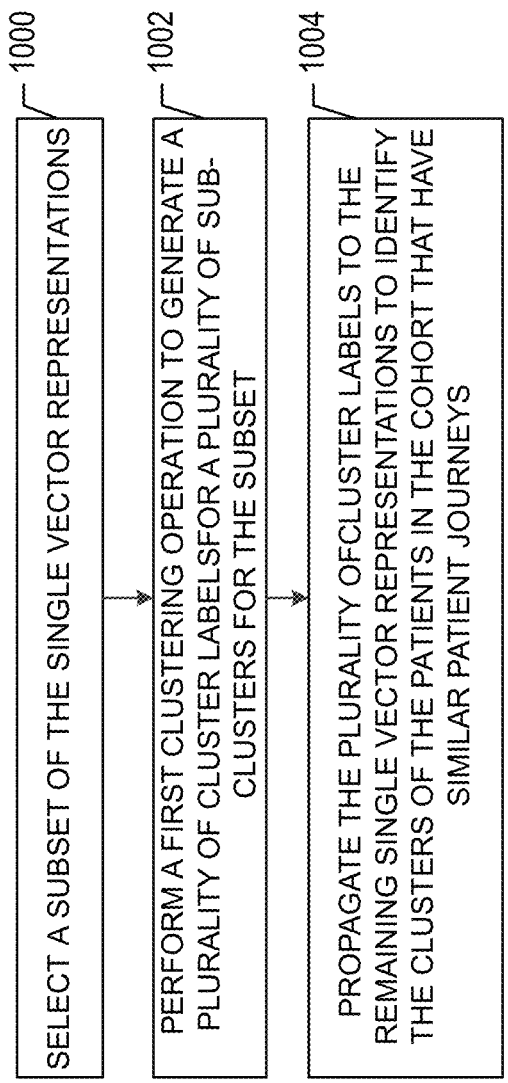
FIG. 10 illustrates an example process for performing a clustering operation, according to certain aspects of the disclosure.

To overcome this problem, the illustrative operations of FIG. 10 can be performed during the clustering operation. For example, at block 1000, clustering engine 246 selects a subset (e.g., a fraction such as a third) of the single vector representations.

At block 1002, clustering engine 246 performs a first clustering operation to generate a plurality of cluster labels for a plurality of sub-clusters for the subset. The first clustering operation may operate on dimensionality-reduced vectors corresponding to the single vector representations of the subset. The first clustering operation may include a k-means clustering operation, a mean-shift clustering operation, a DBSCAN clustering operation, an expectation-maximization clustering operation, an agglomerative hierarchical clustering operation, and/or other suitable clustering operations for identifying clusters of the subset and cluster labels for each cluster.

At block 1004, clustering engine 246 propagates the plurality of cluster labels to the remaining single vector representations (e.g., prior to dimensionality reduction) to identify the clusters of the patients in the pre-identified cohort that have the similar patient journeys. Propagating the cluster labels to the remaining single vector representations may include iteratively enlarging at least some of the plurality of sub-clusters by performing a second clustering operation that assigns, based on the cluster labels, each of the remaining single vector representations to one of the sub-clusters.

Figure 11:
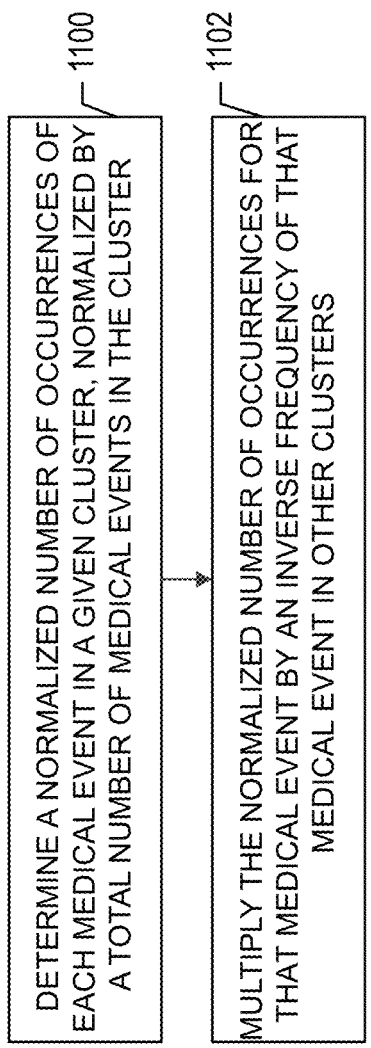
FIG. 11 illustrates an example process for identifying differentiating medical events for a cluster of patients having similar patient journeys, according to certain aspects of the disclosure.

As described above in connection with block 608 of FIG. 6, once the clusters of patients having similar patient journeys 308 have been identified, a cluster profiling operation is performed to identify differentiating medical events for each cluster. FIG. 11 is a flow chart of illustrative operations that can be performed during a cluster profiling operation to identify one or more medical events that are specific to each cluster.

For example, at block 1100, the cluster profiling engine 248 determines a normalized number of occurrences of each medical event in a given one of the clusters, normalized by a total number of medical events in that cluster.

At block 1102, cluster profiling engine 248 multiplies the normalized number of occurrences for that medical event by an inverse frequency of that medical event in other ones of the clusters. In this way, cluster profiling engine 248 considers each medical event found in the entire patient population of the cohort (e.g., all unique medical events found in the ~170 k RA patient cohort of FIG. 7). For each medical event, the number of its occurrences in a given cluster is normalized by the total number medical events in the cluster, in order to adjust for the varying lengths of medical histories from cluster to cluster. The computed frequencies (e.g., term frequency, TF, corresponding to an inverse of the normalized number of occurrences) essentially represent the weight or the importance of the medical events in the cluster. These frequencies are then further adjusted by multiplying them with the inverse frequencies of the medical events appearing in other clusters (e.g., inverse cluster frequency, ICF); the inverse frequencies penalize if a medical event appears in most of the clusters. For example, in the RA diagnosis examples discussed herein, diagnosis of RA is a medical event that is guaranteed to happen for every patient, due to the design of the patient cohort. Thus, the RA diagnosis event would have a relatively high TF. However, since all patients in the cohort have this diagnosis, the ICF of the RA diagnosis event would be very low. Consequently, the product of TF-ICF would be small for all clusters, indicating that this event is not specific to any particular cluster.

In other implementations, rather than using the normalized number of occurrences as described in FIG. 11 to identify distinguishing medical events for each cluster, other operations can be performed such as generating 'word clouds' or performing supervised learning. However, although word clouds provide a simple and quick summary of the topmost frequent medical events in a cluster, the topmost frequent medical events tend to be the same across different clusters, failing to provide the insights into what makes a cluster unique from other clusters. In a supervised learning algorithm to train each patient medical history to a cluster, it would be possible to infer what features from the patient medical history were relatively more important for the cluster classification. However, this type of supervised learning operation would require extensive feature engineering of the patient medical data, which makes it harder to preserve the temporal aspect of the historical data.

Figure 12:
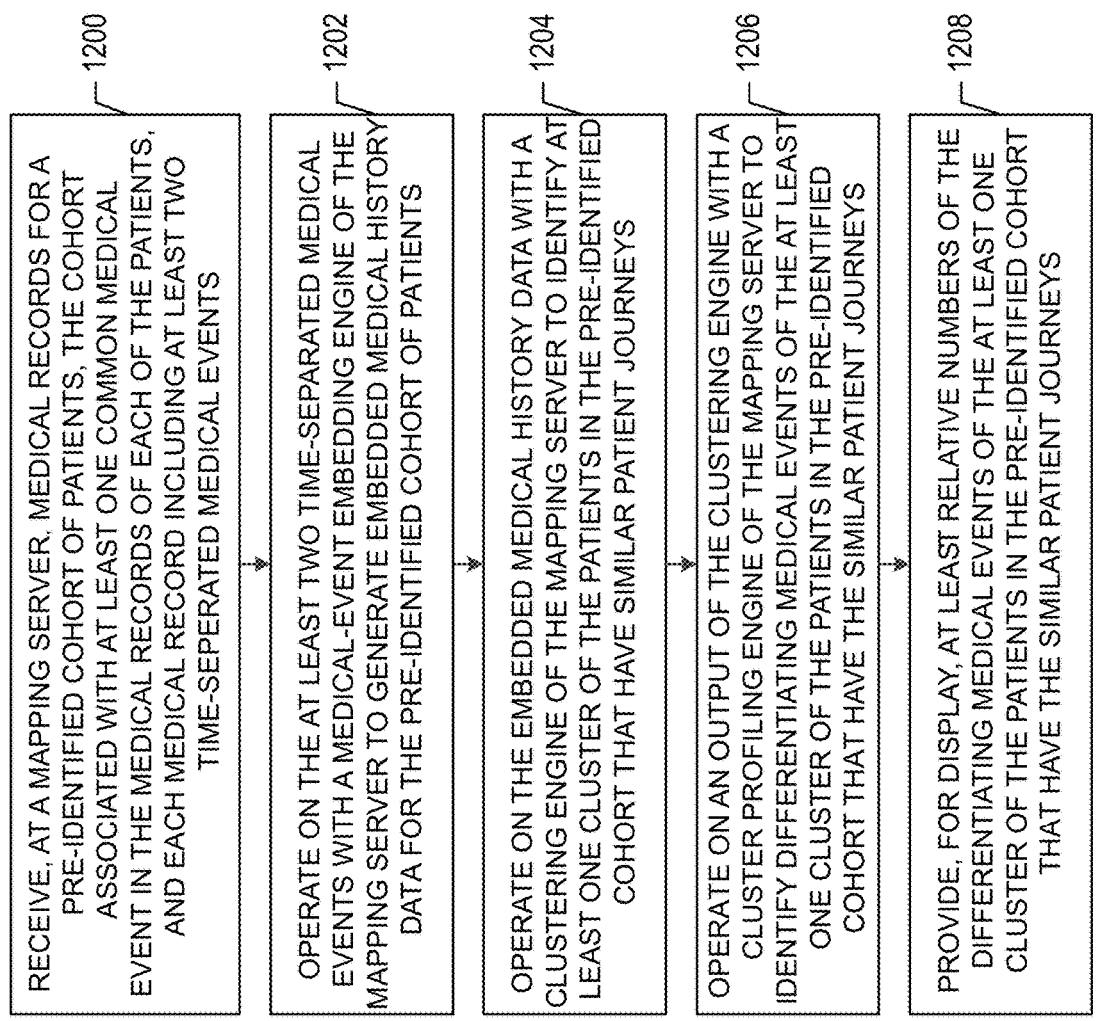
FIG. 12 illustrates another example process for machine-learning based patient journey mapping, according to certain aspects of the disclosure.

FIG. 12 illustrates a flow diagram of another example process for patient journey mapping using machine learning, in accordance with one or more implementations. For explanatory purposes, the process of FIG. 12 is primarily described herein with reference to one or more devices of FIGS. 1 and 2 (particularly with reference to mapping server 130), which may be executed by one or more processors of the mapping server 130 of FIGS. 1 and 2. However, the process of FIG. 12 is not limited to the server 130, and one or more blocks (or operations) of the process may be performed by one or more other components of other suitable devices. Further for explanatory purposes, the blocks of the process of FIG. 12 are described herein as occurring in serial, or linearly. However, multiple blocks of the process of FIG. 12 may occur in parallel. In addition, the blocks of the process of FIG. 12 need not be performed in the order shown and/or one or more blocks of the process of FIG. 12 need not be performed and/or can be replaced by other operations.

At block 1200, a mapping server such as mapping server 130 receives medical records for a pre-identified cohort of patients (see, e.g., cohort 304 of patients 306 in FIG. 3), the cohort associated with at least one common medical event in the medical records of each of the patients, and each medical record including at least two time-separated medical events.

At block 1202, a medical-event embedding engine such as medical-event embedding engine 240 of the mapping server operates on the at least two time-separated medical events to generate embedded medical history data (e.g., vectors and/or single vector representations of generated vectors) as described above in connection with FIGS. 6 and 9 for the pre-identified cohort of patients.

At block 1204, a clustering engine such as clustering engine 246 of the mapping server operates on the embedded medical history data to identify at least one cluster of the patients in the pre-identified cohort that have similar patient journeys (see, e.g., patient journeys 308 of FIG. 3). Operating on the embedded medical history data with the clustering engine of the mapping server may further identify a plurality of other clusters of the patients in the pre-identified cohort that have other similar patient journeys.

At block 1206, a cluster profiling engine, such as cluster profiling engine 248 of the mapping server, operates on an output of the clustering engine to identify differentiating medical events of the at least one cluster of the patients in the pre-identified cohort that have the similar patient journeys. The cluster profiling engine may also operate on the embedded medical history data of the patients in the plurality of other clusters with the cluster profiling engine of the mapping server to identify differentiating medical events of the other clusters of the patients in the pre-identified cohort that have the other similar patient journeys.

At block 1208, the mapping server 130 provides, for display, at least relative numbers of the differentiating medical events of the at least one cluster of the patients in the pre-identified cohort that have the similar patient journeys (see, e.g., FIG. 5). Mapping server 130 may also provide, for display, at least relative numbers of the differentiating medical events of the other clusters of the patients in the pre-identified cohort that have the other similar patient journeys.

As discussed herein, an important difference between medical data from normal text data is that medical events are multidimensional over time, as if a person is reading several different sentences simultaneous in an asynchronous manner. Because of this difference in medical data, hyperparameters that are typically used in word embedding were discovered to be ineffective in the disclosed patient journey mapping systems and operations. To overcome this unexpected challenge, disease-specific hyperparameters (e.g., hyperparameters 255), including the window size, vector dimension, and negative sampling rate are provided for the medical-event embedding engine 240 to tune the medical-event embedding operation. Mapping server 130 may generate the hyperparameters 255 for the medical-event embedding engine using a multidimensionality of the medical records. The multidimensionality of the medical records may include at least two concurrent or overlapping timelines for past diagnoses, medications, lab tests, or procedures.

Figure 13:
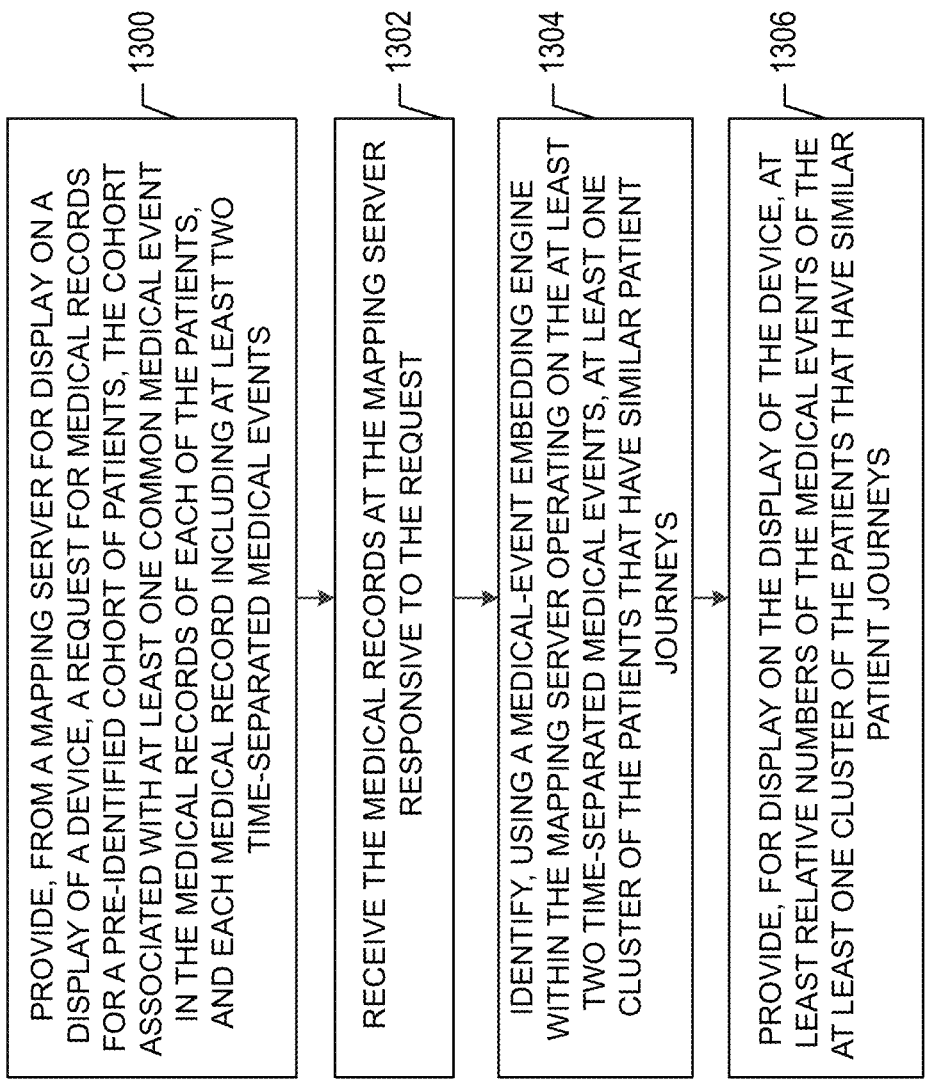
FIG. 13 illustrates an example process for operating a mapping server to provide a user interface, according to certain aspects of the disclosure.

FIG. 13 illustrates a flow diagram of another example process for providing an interface to a mapping server, for patient journey mapping using machine learning, in accordance with one or more implementations. For explanatory purposes, the process of FIG. 13 is primarily described herein with reference to one or more devices of FIGS. 1 and 2 (particularly with reference to mapping server 130), which may be executed by one or more processors of the mapping server 130 of FIGS. 1 and 2. However, the process of FIG. 13 is not limited to the server 130, and one or more blocks (or operations) of the process may be performed by one or more other components of other suitable devices. Further for explanatory purposes, the blocks of the process of FIG. 13 are described herein as occurring in serial, or linearly. However, multiple blocks of the process of FIG. 13 may occur in parallel. In addition, the blocks of the process of FIG. 13 need not be performed in the order shown and/or one or more blocks of the process of FIG. 13 need not be performed and/or can be replaced by other operations.

At block 1300, mapping server 130 provides, for display on a display of a device, a request for medical records for a pre-identified cohort of patients, the cohort associated with at least one common medical event in the medical records of each of the patients, and each medical record including at least two time-separated medical events. The request may be provided via a web interface or an application such as application 222 running on a user device. The request may be provided in, for example, a user interface window that provides a structured input tool for providing identifiers for pre-identified cohorts of patients. The user interface window may include instructions to ensure that the cohort is associated with at least one common medical event in the medical records of each of the patients, and each medical record including at least two time-separated medical events.

At block 1302, the medical records are received (e.g., from medical records database 120) at the mapping server responsive to the request. Receiving the medical records responsive to the request may include receiving, from a user device, identifiers of a pre-identified cohort such as cohort 304 of patient such as patients 306, and obtaining the medical records of the identified patients of the cohort from the medical records database 120.

At block 1304, a medical-event embedding engine, such as medical-event embedding engine 240 of FIG. 2 within the mapping server, operates on the at least two time-separated medical events, to identify at least one cluster of the patients that have similar patient journeys. Identifying the at least one cluster may include one or more of the operations described above in connection with, for example, FIGS. 6 through 12.

At block 1306, the mapping server provides, for display on the display of the device, at least relative numbers of the medical events of the at least one cluster of the patients that have similar patient journeys. For example, the mapping server may provide raw numbers for display, a formatted table or chart, or a graphical representation such as the graphical representation of FIG. 5. The mapping server may provide the output in a packaged format, such as in a JPEG, GIF, or PDF image, or in a format specific to a particular display technology.

Hardware Overview

Figure 14:
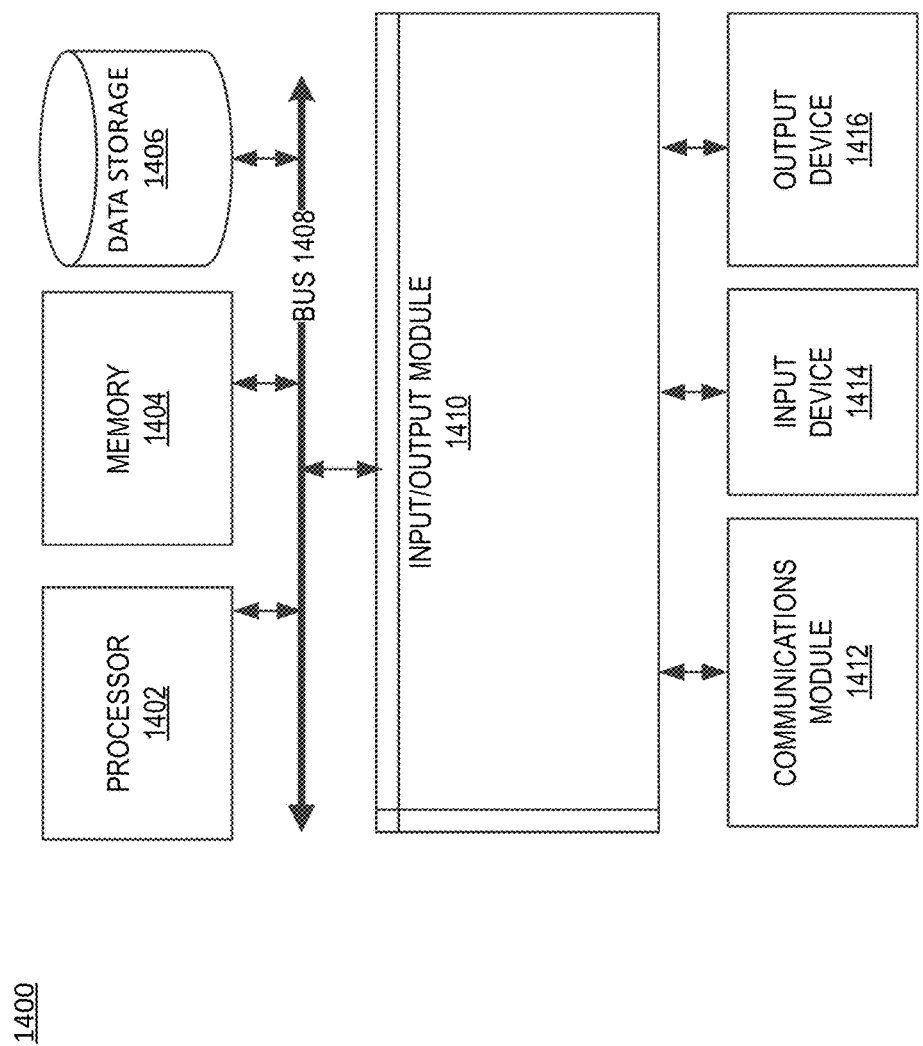
FIG. 14 is a block diagram illustrating an example computer system with which the user device or mapping server of FIG. 2 can be implemented.

FIG. 14 is a block diagram illustrating an exemplary computer system 1400 with which the user device 110 or mapping server 130 of FIG. 1 can be implemented. In certain aspects, the computer system 1400 may be implemented using hardware or a combination of software and hardware, either in a dedicated server, or integrated into another entity, or distributed across multiple entities.

Computer system 1400 includes a bus 1408 or other communication mechanism for communicating information, and a processor 1402 (e.g., an implementation of processor 212 or 236) coupled with bus 1408 for processing information. By way of example, the computer system 1400 may be implemented with one or more processors 1402. Processor 1402 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable entity that can perform calculations or other manipulations of information.

Computer system 1400 can include, in addition to hardware, code that creates an execution environment for the computer program in question, e.g., code that constitutes processor firmware, a protocol stack, a database management system, an operating system, or a combination of one or more of them stored in an included memory 1404 (e.g., memory 220 or 232), such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device, coupled to bus 1408 for storing information and instructions to be executed by processor 1402. The processor 1402 and the memory 1404 can be supplemented by, or incorporated in, special purpose logic circuitry.

The instructions may be stored in the memory 1404 and implemented in one or more computer program products, i.e., one or more modules of computer program instructions encoded on a computer readable medium for execution by, or to control the operation of, the computer system 1400, and according to any method well known to those of skill in the art, including, but not limited to, computer languages such as data-oriented languages (e.g., SQL, dBase), system languages (e.g., C, Objective-C, C++, Assembly), architectural languages (e.g., Java, .NET), and application languages (e.g., PHP, Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, multiparadigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, wirth languages, and xml-based languages. Memory 1404 may also be used for storing temporary variable or other intermediate information during execution of instructions to be executed by processor 1402.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

Computer system 1400 further includes a data storage device 1406, such as a magnetic disk or optical disk, coupled to bus 1408 for storing information and instructions. Computer system 1400 may be coupled via input/output module 1410 to various devices. The input/output module 1410 can be any input/output module. Exemplary input/output modules 1410 include data ports such as USB ports. The input/output module 1410 is configured to connect to a communications module 1412. Exemplary communications modules 1412 (e.g., communications modules 218 and 238) include networking interface cards, such as Ethernet cards and modems. In certain aspects, the input/output module 1410 is configured to connect to a plurality of devices, such as an input device 1414 (e.g., input device 216) and/or an output device 1416 (e.g., output device 214). Exemplary input devices 1414 include a keyboard and a pointing device (e.g., a mouse or a trackball), by which a user can provide input to the computer system 1400. Other kinds of input devices 1414 can be used to provide for interaction with a user as well, such as a tactile input device, visual input device, audio input device, or brain-computer interface device. For example, feedback provided to the user can be any form of sensory feedback (e.g., visual feedback, auditory feedback, or tactile feedback), and input from the user can be received in any form, including acoustic, speech, tactile, or brain wave input. Exemplary output devices 1416 include display devices, such as a LCD (liquid crystal display) monitor, for displaying information to the user.

According to one aspect of the present disclosure, user device 110 or mapping servers 130 can be implemented using a computer system 1400 in response to processor 1402 executing one or more sequences of one or more instructions contained in memory 1404. Such instructions may be read into memory 1404 from another machine-readable medium, such as data storage device 1406. Execution of the sequences of instructions contained in main memory 1404 causes processor 1402 to perform the process steps described herein. One or more processors in a multi-processing arrangement may also be employed to execute the sequences of instructions contained in memory 1404. In alternative aspects, hard-wired circuitry may be used in place of, or in combination with, software instructions to implement various aspects of the present disclosure. Thus, aspects of the present disclosure are not limited to any specific combination of hardware circuitry and software.

Various aspects of the subject matter described in this specification can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the subject matter described in this specification), or any combination of one or more such back end, middleware, or front end components. The components of the system can be interconnected by any form or medium of digital data communication (e.g., a communication network). The communication network (e.g., network 150) can include, for example, any one or more of a LAN, a WAN, the Internet, and the like. Further, the communication network can include, but is not limited to, for example, any one or more of the following network topologies, including a bus network, a star network, a ring network, a mesh network, a star-bus network, a tree or hierarchical network, or the like. The communications modules can be, for example, modems or Ethernet cards.

Computer system 1400 can include clients and servers. A client and server are generally remote from each other and typically interact through a communication network. The relationship of client and server arises by virtue of computer programs running on the respective computers and having a client-server relationship to each other. Computer system 1400 can be, for example, and without limitation, a desktop computer, laptop computer, or tablet computer. Computer system 1400 can also be embedded in another device, for example, and without limitation, a mobile telephone, a PDA, a mobile audio player, a Global Positioning System (GPS) receiver, a video game console, and/or a television set top box.

The term "machine-readable storage medium" or "computer readable medium" as used herein refers to any medium or media that participates in providing instructions to processor 1402 for execution. Such a medium may take many forms, including, but not limited to, non-volatile media, volatile media, and transmission media. Non-volatile media include, for example, optical or magnetic disks, such as data storage device 1406. Volatile media include dynamic memory, such as memory 1404. Transmission media include coaxial cables, copper wire, and fiber optics, including the wires that comprise bus 1408. Common forms of machine-readable media include, for example, a floppy disk, a flexible disk, a hard disk, magnetic tape, any other magnetic medium, a CD-ROM, a DVD, any other optical medium, punch cards, paper tape, any other physical medium with patterns of holes, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter effecting a machine-readable propagated signal, or a combination of one or more of them.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

To the extent that the term "include", "have", or the like is used in the description or the claims, such term is intended to be inclusive in a manner similar to the term "comprise" as "comprise" is interpreted when employed as a transitional word in a claim. The word "exemplary" is used herein to mean "serving as an example, instance, or illustration". Any embodiment described herein as "exemplary" is not necessarily to be construed as preferred or advantageous over other embodiments.

A reference to an element in the singular is not intended to mean "one and only one" unless specifically stated, but rather "one or more". All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While this specification contains many specifics, these should not be construed as limitations on the scope of what may be claimed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable sub combination. Moreover, although features may be described above as acting in certain combinations and even initially claimed as such, one or more features from a claimed combination can, in some cases, be excised from the combination, and the claimed combination may be directed to a sub combination or variation of a sub combination.

The subject matter of this specification has been described in terms of particular aspects, but other aspects can be implemented and are within the scope of the following claims. For example, while operations are depicted in the drawings in a particular order, this should not be understood as requiring that such operations be performed in the particular order shown or in sequential order, or that all illustrated operations be performed, to achieve desirable results. The actions recited in the claims can be performed in a different order and still achieve desirable results. As one example, the processes depicted in the accompanying figures do not necessarily require the particular order shown, or sequential order, to achieve desirable results. In certain circumstances, multitasking and parallel processing may be advantageous. Moreover, the separation of various system components in the aspects described above should not be understood as requiring such separation in all aspects, and it should be understood that the described program components and systems can generally be integrated together in a single software product or packaged into multiple software products. Other variations are within the scope of the following claims.

What is claimed is:

1. A computer-implemented method, comprising:
   defining, by a processor of a mapping server, a pre-identified cohort of patients by identifying a reduced set of patients having a common medical event in a medical record of each patient, the set of patients reduced (i) based on a sequence of events in the medical record of each patient, and (ii) by excluding a patient based on a diagnosis in the medical record of the patient;
   randomizing, by the processor of the mapping server, an order of two or more medical events from the medical record of each patient in the pre-identified cohort, the medical record including two time-separated medical events in at least two overlapping timelines including past diagnoses, medications, lab tests and procedures for the pre-identified cohort of patients to a medical-event embedding engine of the mapping server;
   providing, by the processor of the mapping server, the two or more medical events from the medical record of each patient in the pre-identified cohort to the medical-event embedding engine of the mapping server, the medical-event embedding engine having parameters trained by a neural network model executed by the processor of the mapping server to cause the medical-event embedding engine to generate an output vector corresponding to a medical event in an input medical record, the processor of the mapping server configured to perform computations in parallel using the neural network model;
   generating, by the processor of the mapping server, a vector with the medical-event embedding engine by operating on the two or more medical events for each of the patients in the pre-identified cohort, each vector corresponding to a medical event in the medical record of one of the patients in the pre-identified cohort;
   generating, by the processor of the mapping server, a weight for each vector using a timestamp for the medical event corresponding to the vector, wherein a vector with a more recent timestamp has a greater weight than a vector with a less recent timestamp;

combining, with the processor of the mapping server, the vector for each patient in the pre-identified cohort to form a single vector representation of a medical history for each patient in the pre-identified cohort by generating a weighted average of the vectors using the weight for each vector;

reducing, by the processor of the mapping server, a number of dimensions of each single vector representation to reduce a computational complexity of a clustering operation performed by the processor of the mapping server;

identifying, by the processor of the mapping server, with a clustering engine of the mapping server, multiple clusters of the patients in the pre-identified cohort that have similar patient journeys by performing the clustering operation on the single vector representations;

identifying, by the processor of the mapping server, with a cluster profiling engine of the mapping server, a differentiating medical event of each of the clusters by performing a cluster-profiling operation using an output of the clustering engine and the medical records of the patients in the clusters; and providing, by the processor and for display, at least relative numbers of the differentiating medical event in at least one of the clusters.

2. The method of claim 1, further comprising modifying the medical record prior to providing the two or more medical events from the medical record for each patient in the pre-identified cohort to the medical-event embedding engine, wherein modifying the medical record includes at least one of: mapping a set of codes in the medical record to a set of generic identifiers, and removing duplicate medical events in a pre-defined time period from the medical record.

3. The method of claim 1, wherein the common medical event includes a first diagnosis in the medical record of each patient, wherein the diagnosis in the medical record of each patient is a second diagnosis different from the first diagnosis, and wherein the sequence of events comprises a sequence of events spanning at least one year before and one year after the first diagnosis.

4. The method of claim 1, wherein the common medical event includes a treatment with a drug, and wherein the sequence of events comprises treatment with the drug after a diagnosis.

5. The method of claim 1, further comprising identifying the pre-identified cohort by:

identifying a first subset of patients with a number of diagnosis claims for a particular condition in the medical record;

identifying a second subset of the first subset having an age range in the medical record;

identifying a third subset of the second subset having a medical history range in the medical record; and identifying the pre-identified cohort by excluding misdiagnosed patients from the third subset.

6. The method of claim 5, wherein excluding the misdiagnosed patients comprises identifying an additional diagnosis of a different condition subsequently to the diagnosis with the particular condition.

7. The method of claim 1, further comprising generating a weight for each vector using a prior medical history for the patient corresponding to the vector.

8. The method of claim 1, wherein the clustering operation includes:

selecting a subset of the single vector representation;

performing a first clustering operation to generate a plurality of cluster labels for a plurality of sub-clusters for the subset; and propagating the plurality of cluster labels to the single vector representation to identify the clusters of the patients in the pre-identified cohort that have the similar patient journeys.

9. The method of claim 8, wherein performing the first clustering operation comprises performing the first clustering operation on dimensionality-reduced vectors corresponding to the single vector representations of the subset, and wherein propagating the cluster labels to the single vector representations comprises iteratively enlarging at least some of the plurality of sub-clusters by performing a second clustering operation that assigns, based on the cluster labels, each of the single vector representation to one of the sub-clusters.

10. The method of claim 1, wherein the cluster-profiling operation includes identifying one or more medical events that are specific to each cluster.

11. The method of claim 10, wherein identifying the medical events that are specific to each cluster includes:

determining a normalized number of occurrences of each medical event in a given one of the clusters, normalized by a total number of the medical events in that cluster; and multiplying the normalized number of occurrences for that medical event by an inverse frequency of that medical event in other ones of the clusters.

12. The method of claim 5, wherein excluding the misdiagnosed patients comprises ruling out an initial diagnosis based on a procedure, a lab test, or another medical event in the medical records.

* * * * *